(12) United States Patent
Chan et al.

(10) Patent No.: US 8,754,257 B2
(45) Date of Patent: *Jun. 17, 2014

(54) PHARMACEUTICAL-GRADE FERRIC ORGANIC COMPOUNDS, USES THEREOF AND METHODS OF MAKING SAME

(71) Applicant: GloboAsia, LLC, Rockville, MD (US)

(72) Inventors: Keith Chan, Rockville, MD (US); Winston Town, Hong Kong (CN)

(73) Assignee: Panion & BF Biotech Inc. (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/661,558

(22) Filed: Oct. 26, 2012

(65) Prior Publication Data

US 2013/0052261 A1 Feb. 28, 2013

Related U.S. Application Data

(63) Continuation of application No. 13/289,048, filed on Nov. 4, 2011, now Pat. No. 8,299,298, which is a continuation of application No. 12/064,058, filed as application No. PCT/US2006/032385 on Aug. 18, 2006, now Pat. No. 8,093,423, and a continuation-in-part of application No. 11/206,981, filed on Aug. 18, 2005, now Pat. No. 7,767,851, which is a continuation-in-part of application No. PCT/US2004/004646, filed on Feb. 18, 2004.

(60) Provisional application No. 60/709,511, filed on Aug. 19, 2005, provisional application No. 60/462,684, filed on Apr. 15, 2003, provisional application No. 60/447,690, filed on Feb. 19, 2003.

(51) Int. Cl.
*C07C 63/36* (2006.01)

(52) U.S. Cl.
USPC .............................. 562/590; 562/582; 514/502

(58) Field of Classification Search
None
See application file for complete search history.

(56) References Cited

U.S. PATENT DOCUMENTS

| | | | |
|---|---|---|---|
| 3,591,616 A | 7/1971 | Baldt | |
| 4,180,567 A | 12/1979 | Herb | |
| 4,689,322 A | 8/1987 | Kulbe et al. | |
| 4,970,079 A | 11/1990 | Hem et al. | |
| 5,206,265 A | 4/1993 | Vidic et al. | |
| 5,707,980 A | 1/1998 | Knutson et al. | |
| 5,753,706 A | 5/1998 | Hsu | |
| 6,887,897 B2 | 5/2005 | Walsdorf, Sr. et al. | |
| 6,903,235 B2 | 6/2005 | Hsiao et al. | |
| 7,767,851 B2 * | 8/2010 | Kwok et al. | 562/590 |
| 8,093,423 B2 * | 1/2012 | Chan et al. | 562/590 |
| 8,299,298 B2 * | 10/2012 | Chan et al. | 562/590 |
| 2005/0080283 A1 | 4/2005 | Hsiao et al. | |
| 2006/0020026 A1 | 1/2006 | Kwok et al. | |
| 2008/0274210 A1 | 11/2008 | Chan et al. | |
| 2009/0186939 A1 | 7/2009 | Chan et al. | |
| 2009/0326060 A1 | 12/2009 | Chan et al. | |
| 2010/0217025 A1 | 8/2010 | Kwok et al. | |

FOREIGN PATENT DOCUMENTS

| | | |
|---|---|---|
| AU | 199854419 | 7/1998 |
| AU | 723901 | 11/2000 |
| AU | 2004213819 | 8/2005 |
| AU | 2006279333 | 3/2008 |
| AU | 2007210090 | 7/2008 |
| AU | 2007210096 | 7/2008 |
| AU | 2004213819 | 12/2009 |
| AU | 2004216819 | 12/2009 |
| CA | 2272711 | 5/1999 |
| CA | 2516471 | 8/2005 |
| CA | 2619591 | 2/2008 |
| CA | 2272711 | 4/2008 |
| CA | 2640673 | 7/2008 |
| CA | 2640974 | 7/2008 |
| CN | 1315174 | 10/2001 |
| CN | 03157490.4 | 9/2003 |
| CN | 1446790 | 10/2003 |
| CN | 1600302 | 3/2005 |
| CN | 1751056 A | 3/2006 |
| CN | 101019848 A | 8/2007 |
| CN | 101235186 A | 8/2008 |
| CN | 101374416 | 2/2009 |
| CN | 101378658 | 3/2009 |
| DE | 1131360 | 6/1962 |
| EA | 200501322/26 | 9/2005 |
| EA | 200800593126 | 3/2008 |
| EA | 010028 | 6/2008 |
| EP | 0308362 | 3/1989 |
| EP | 0600347 | 6/1994 |
| EP | 0959878 | 12/1999 |
| EP | 1601680 | 12/2005 |
| EP | 1931689 | 6/2008 |

(Continued)

OTHER PUBLICATIONS

PCT International Search Report for GloboAsia, LLC et al., International Application No. PCT/US2007/002151, filed Jan. 26, 2007, Dated Nov. 26, 2007.

(Continued)

*Primary Examiner* — Yevegeny Valenrod
(74) *Attorney, Agent, or Firm* — Law Offices of Albert Wai-Kit Chan, PLLC

(57) ABSTRACT

The present invention discloses a pharmaceutical-grade ferric organic compounds, including ferric citrate, which are soluble over a wider range of pH, and which have a large active surface area. A manufacturing and quality control process for making a pharmaceutical-grade ferric citrate that consistently complies with the established Manufacture Release Specification is also disclosed. The pharmaceutical-grade ferric organic compounds are suitable for treating disorders characterized by elevated serum phosphate levels.

8 Claims, 14 Drawing Sheets

(56) References Cited

FOREIGN PATENT DOCUMENTS

| | | |
|---|---|---|
| EP | 101235186 A | 6/2008 |
| EP | 0959878 | 7/2008 |
| EP | 1978807 | 10/2008 |
| EP | 1978808 | 10/2008 |
| GB | 1224589 | 3/1971 |
| GB | 1226394 | 3/1971 |
| GB | 2212396 A | 7/1989 |
| HK | 1077580 A | 2/2006 |
| ID | WO2005002228 | 8/2005 |
| IL | 170385 | 8/2005 |
| IL | 130041 | 12/2005 |
| IL | 189583 | 2/2008 |
| IL | 193099 | 7/2008 |
| IL | 192545 | 8/2008 |
| IN | 00944/MUMNP/2005 | 8/2005 |
| IN | 393/MUMNP/20008 A | 3/2008 |
| IN | 1413/MUMNP/2008 | 7/2008 |
| IN | 1414/MUMNP/2008 | 7/2008 |
| IN | 244119 | 11/2010 |
| JP | 8198760 A | 8/1996 |
| JP | 2007-133978 | 11/1997 |
| JP | 2001-506262 | 5/2001 |
| JP | 2006-518391 | 8/2006 |
| JP | 2008-552431 | 7/2008 |
| JP | 2008-552435 | 7/2008 |
| JP | 4173553 | 8/2008 |
| JP | 2009-24341 | 2/2009 |
| JP | 2009-504777 | 2/2009 |
| JP | 2009-525276 | 7/2009 |
| KR | 464504 | 12/2004 |
| KR | 10-2005-0107428 | 11/2005 |
| KR | 10-2008-70106131 | 4/2008 |
| KR | 10-2008-0094013 | 10/2008 |
| KR | 10-2008-0106506 | 12/2008 |
| LK | 13792 | 8/2008 |
| ML | PI2006-3971 | 8/2006 |
| MX | 207250 | 3/2002 |
| MX | PA05008784 A | 5/2006 |
| MX | MX/A/2008/002360 | 2/2008 |
| NO | 19992936 | 6/1999 |
| NO | 327148 | 5/2009 |
| NZ | 336060 | 6/1999 |
| NZ | 541991 | 2/2004 |
| NZ | 566743 | 3/2008 |
| NZ | 541991 | 2/2009 |
| NZ | 566743 | 11/2010 |
| PG | PG/P/05/00029 | 8/2005 |
| PH | 1-2005-501521 | 8/2005 |
| RU | 2188033 | 8/2002 |
| SG | 200505259-2 | 8/2005 |
| SG | 114272 | 7/2007 |
| SU | 142643 | 3/1961 |
| TL | 061003938 | 8/2006 |
| TW | 86104116 | 3/1997 |
| TW | 93103743 | 2/2004 |
| TW | 259772 B | 8/2006 |
| TW | 95130373 | 8/2006 |
| VN | 1-2005-01292 | 9/2005 |
| VN | 8033 | 11/2009 |
| WO | WO 98/26776 | 6/1995 |
| WO | WO 2004/074444 | 9/2004 |
| WO | WO 2007/022435 | 2/2007 |
| WO | WO 2007/089571 | 8/2007 |
| WO | WO 2007/089577 | 8/2007 |
| WO | WO 2011/011541 A1 | 1/2011 |

OTHER PUBLICATIONS

PCT Written Opinion of the International Searching Authority for GloboAsia, LLC et al., International Application No. PCT/US2007/002151, filed Jan. 26, 2007, Dated Nov. 26, 2007.

Austrian Written Opinion for GloboAsia, LLC, Singapore Application No. 200505259-2, filed Aug. 18, 2005, Dated Jul. 7, 2006.

Austrian Examination Report for GloboAsia, LLC, Singapore App'l No. 200505259-2, filed Aug. 18, 2005, Dated Mar. 16, 2007.

Canadian Office Action for Chen Hsing Hsu, Canadian Application No. 2,272,711, filed May 26, 1999, Dated Jan. 18, 2005.

Canadian Office Action for Chen Hsing Hsu, Canadian Application No. 2,272,711, filed May 26, 1999, Dated Dec. 22, 2005.

Canadian Office Action for Chen Hsing Hsu, Canadian Application No. 2,272,711, May 26, 1999, Dated Sep. 15, 2006.

Canadian Notice of Allowance for Chen Hsing Hsu, Canadian Application No. 2,272,711, filed May 26, 1999, Dated Aug. 10, 2007.

Chinese Office Action for GloboAsia, LLC, Chinese App'l No. 200480004726.7, filed Aug. 19, 2005, dated Nov. 3, 2006.

Chinese Office Action for GloboAsia, LLC, Chinese Chinese App'l No. 200480004726.7, filed Aug. 19, 2005, Dated Aug. 17, 2007.

Ramirez et al., 1986, "The Absorption of Dietary Phosphorus and Calcium in Hemodialysis Patients", Kidney International, vol. 30: 753-759.

Rehm et al., 1940, "The Effect of Ferric Chloride on the Utilization of Calcium and Phosphorous in the Animal Body", Journal of Nutrition, vol. 19: 213-222.

Reinhardt et al., 1984, "A Microassay for 1,25-Dihydroxyvitamin D Not Requiring High Performance Liquid Chromatography: Application to Clinical Studies", Journal of Clinical Endocrinology and Metabolism, vol. 58(1): 91-98.

Slaptopolsky et al., 1971, "On the Pathogenesis of Hyperparathyroidism in Chronic Experimental Renal Insufficiency in the Dog", Journal of Clinical Investigations, vol. 50: 492-499.

Slaptopolsky et al., 1995, "Phosphate (PO) Restriction Prevents Parathyroid Cell Growth in Uremic Rats and High Phosphate Directly Stimulates PTH Secretion in Tissue Culture", American Society of Nephrology, vol. 6: 971.

Spiro et al., 1967, "The Hydrolytic Polymerization of Ferric Citrate. T. The Chemistry of the Polymer", Journal of the American Chemical Society, vol. 89: 5555-5559.

Terato et al., 1972, "Studies on Intestinal Absorption of Iron. I. Effects of Sugars, Polyalcohols and Organic Acids on Hydrolytic Polymerization of Iron", Journal of the Pharmaceutical Society of Japan, vol. 92(10):1247-1251.

The Ferric Citrate Study Group, 2007, "A Phase II Randomized, Double-Blind, Placebo-Controlled, Dose-Ranging Study of Ferric Citrate (FC) on Serum Phosphorous Levels" (Abstract of Patent application to be filed).

The Ferric Citrate Study Group, 2007, "Ferric Citrate: Effects on Iron Parameters, Hematocrit, and Hemoglobin in End-Stage Renal Disease Patients" (Abstract of Patent application to be filed).

The Ferric Citrate Study Group, 2006, "A Phase II Randomized, Double-Blind, Placebo-Controlled, Dose-Ranging Study of Ferric Citrate (FC) on Serum Phosphorous Levels" (Abstract of Patent application to be filed).

The Ferric Citrate Study Group, 2006, "Effects on Iron Parameters in End-Stage Renal Disease Patients" (Abstract of Patent application to be filed).

Thomas, W.C., 1982, "Trace Metal-Citric Acid Complexes as Inhibitors of Calcification and Crystal Formation", Proc. Soc. Exp. Biol. Med., vol. 170, No. 3, 321-327.

Webster'S II New Riverside University Dictionary, 1984, Riverside Publishing Company, p. 763.

Yamamoto et al., 1995, "Interaction between Various Phosphate Compounds and Iron Compounds Containing Sodium Ferrous Citrate", Shinyaku & Rinsho, vol. 44(5):9-15. (w /English Abstract).

PCT International Search Report for Chen Hsing Hsu, International Application No. PCT/US1998/020977, filed Nov. 14, 1997, Dated Feb. 10, 1998.

PCT Written Opinion of the International Searching Authority for Chen Hsing Hsu, International Application No. PCT/US1998/020977, filed Nov. 14, 1997, Dated Nov. 12, 1998.

PCT International Preliminary Examination Report for Chen Hsing Hsu, International Application No. PCT/US1998/020977, filed Nov. 14, 1997, Dated Mar. 2, 1999.

Chinese Office Action for Hsaio et al., Chinese Application No. 03157490.4, filed Sep. 22, 2003, Dated Jul. 25, 2005.

European Decision to Grant a European Patent Pursuant to Article 97(1) EPC for Chen Hsing Hsu, European App'l No. 97948333.6, filed Nov. 14, 1997, Dated Jun. 12, 2008.

(56) References Cited

OTHER PUBLICATIONS

Japanese Decision to Grant for Chen Hsing Hsu, Japanese Application No. 10-527705, filed Jun. 15, 1999, Dated Jul. 16, 2008.
Norwegian Office Action for Chen Hsing Hsu, Norwegian Application No. 19992936, filed Jun. 16, 1999, Dated Apr. 17, 2008.
Taiwan Office Action for Chen Hsing Hsu, Taiwanese App'l No. 86104116, filed Mar. 31, 1997, Dated Apr. 13, 1999.
Taiwan Patent Re-Examination Notice for Chen Hsing Hsu, Taiwanese App'l No. 86104116, filed Mar. 31, 1997, Dated Aug. 10, 1999.
Taiwan Office Action for Chen Hsing Hsu, Taiwanese App'l No. 86104116, filed Mar. 31, 1997, Dated Aug. 30, 1999.
Taiwan Office Action for Kwok et al., Taiwan Application No. 93103743, filed Feb. 17, 2004, Dated Aug. 3, 2006.
Taiwan Office Action for Kwok et al., Taiwan Application No. 93103743, filed Feb. 17, 2004, Dated Feb. 1, 2007.
Taiwan Notice of Allowance for Hsiao et al., Taiwan App'l No. 092124445, filed Sep. 4, 2003, Dated Jun. 16, 2006.
Barer et al., 1940, "The Effect of Iron on Phosphorous, Calcium, and Nitrogen Metabolism", Journal of Laboratory & Clinical Medicine, vol. 26: 351-360.
Block et al., Jun. 2000, "Re-Evaluation of Risks Associated with Hyperphosphatemia and Hyperparathyroidism in Dialysis Patients: Recommendations for a Change in Management", American Journal of Kidney Diseases, vol. 35 (6) :1226-1237.
Ghosh, Amit Kumar, 2002, "Letters and Replies: Efficacy of Ferric Citrate as a Phosphate-binding Agent in End-stage Renal Failure", Nephrology Dialysis Transplantation, vol. 17:1354-1355.
Israeli Preliminary Office Action, Dec. 3, 2009, for Israeli App'l No. IL 193099, filed Jul. 28, 2008.
Mexican Examination Report, Aug. 5, 2009, for Mexican App'l No. PA/a/2005/008784, filed Aug. 18, 2005.
Malaysian Substantive Examination Adverse Report, Mar. 27, 2009, for Malaysian App'l No. PI 20063971, filed Aug. 18, 2006.
Papua New Guinea Search and Examination Report, May 5, 2009, for Papua New Guinea App'l No. PG/P/2005/00029, filed Aug. 22, 2005.
Philippine Examination Report, Dec. 16, 2008, for Philippine App'l No. 1-2005-501521, filed Aug. 19, 2005.
Taiwan Office Action, Mar. 18, 2007, for Kwok et al., Taiwan App'l No. TW 093103743, filed Feb. 17, 2004.
Vietnam Notification for Kwok et al., Apr. 28, 2009, Vietnam App'l No. 1-2005-01292, filed Feb. 18, 2004.
Vietnam Notification on Result of Substantive Examination, Sep. 29, 2009, for Vietnam App'l No. VN-1-2005-01292, filed Feb. 18, 2004.
Niecestro, Robert, Apr. 21, 2007, "Ferric Citrate for the Treatment of Hyperphosphatemia in ESRD", 2007 World Congress of Nephrology Conference, pp: 160-161.
Niecestro et al., 2006, "A Randomized, Double-Blind, Placebo-Controlled, Dose-Ranging Study of the Effects of Ferric Citrate on Serum Phosphorous Levels in Patients with End Stage Renal Disease (ESRD)." (PowerPoint Presentation made at Renal Week of the American Society of Nephrology conference on Nov. 18, 2006).
Eurasian Decision to Grant a Eurasian Patent for GloboAsia, LLC, Eurasian App'l No. 200501322, filed Feb. 18, 2004, Dated Mar. 6, 2008.
Israeli Office Action for Chen-Hsing Hsu, Israeli Application No. 130041, filed May 19, 1999, Dated Nov. 16, 2000.
Israeli Office Action for GloboAsia, LLC, Israeli Application No. 170382, filed Aug. 18, 2005, Dated Apr. 18, 2008.
Japanese Office Action for Chen Hsing Hsu, Japanese Application No. 10-527705, filed Jun. 15, 1999, Dated Nov. 22, 2006.
Japanese Office Action for Chen Hsing Hsu, Japanese Publication No. 2001-506262, filed May 15, 2001, Dated Dec. 5, 2006.
Japanese Office Action for Chen Hsing Hsu, Japanese Application No. 10-527705, filed Jun. 15, 1999, Dated Aug. 29, 2007.
Korean Office Action for Chen Hsing Hsu, Korean Application No. 10-1999-7005186, filed Jun. 10, 1999, Dated Jun. 22, 2004.
Korean Notice of Decision for Patent for Chen Hsing Hsu, Korean Application No. 10-1999-7005186, filed Jun. 10, 1999, Dated Oct. 26, 2004.
New Zealand Office Action for GloboAsia, LLC, New Zealand Application No. 541991, filed Sep. 19, 2005, Dated Jul. 25, 2007.
New Zealand Examiner's Report for Chen Hsing Hsu, New Zealand Application No. 336060, filed Jun. 1, 1999, Dated Jul. 16, 1999.
U.S. Office Action for Kwok et al., U.S. Appl. No. 11/206,981, filed Aug. 18, 2005, Dated Mar. 3, 2007.
U.S. Office Action for Kwok et al., U.S. Appl. No. 11/206,981, filed Aug. 18, 2005, Dated Dec. 6, 2007.
Almaden et al., 1995, "High Phosphorous Directly Stimulates PTH Secretion by Human Parathyroid Tissue", Journal of the American Society of Nephrology, vol. 6: 957.
American Chemical Society Feb. 6, 1961, "Ferric Citrate", Chemical Abstracts, vol. 55 (3): 3939d.
Anjyo et al., 1944, "Medication Advice for Patients with Hypoferric Anemia", Yakkyoku, vol. 45(5): 55-59. (w/English Abstract).
Brock et al., 1934, "Rickets in Rats by Iron Feeding", Journal of Pediatrics, vol. 4:442-453.
Clarkson et al., 1966, "The Effect of a High Intake of Calcium Carbonate in Normal Subjects and Patients with Chronic Renal Failure", Clinical Science, vol. 30: 425-438.
Coburn et al., 1973, "Study of Intestinal Absorption of Calcium in Patients with Renal Failure", Kidney International, vol. 3: 264-272.
Coburn et al., 1973, "Intestinal Absorption of Calcium and the Effect of Renal Insufficiency", Kidney International, vol. 4: 96-104.
Cox et al., 1931, "The Effects of High Doses of Aluminum and Iron on Phosphorous Metabolism", Journal of Biological Chemistry, vol. 92: Xi-Xii.
Cullen et al., 2008, "A 28-Day Toxicity Study of KRX-0502 (Ferric Citrate) in Rats by Dietary Administration, Keryx Biopharmaceuticals, Inc." (poster presentation).
Cullen et al., 2008, "A 28-Day Toxicity Study of KRX-0502 (Ferric Citrate) in Rats by Dietary Administration, Keryx Biopharmaceuticals, Inc." (abstract only).
Deobald et al., 1935, "The Effect of Feeding High Amounts of Soluble Iron and Aluminum Salts", American Journal of Physiology, vol. 111: 118-123.
Editorial [No Author], 1986, "Citrate for Calcium Nephrolithiasis," The Lancet, vol. 330, Issue 8487: 955.
Gimenez et al., 1982, "Prevention of Phosphate-induced Progression of Uremia in Rats by 3-phosphocitric Acid", Kidney International, vol. 22: 36-41.
Gutteridge J.M.C., 1991, "Hydroxyl Radical Formation from the Auto-Reduction of a Ferric Citrate Complex", Free Radical Biology and Medicine, vol. 11(4):401-406.
Haut et al., 1980, "Renal Toxicity of Phosphate in Rats", Kidney International, vol. 17: 722-731.
Hollis Bruce W., 1986, "Assay of Circulating 1,25-Dihydroxyvitamin D Involving a Novel Single-Cartridge Extraction and Purification Procedure", Clinical Chemistry, vol. 32: 2060-2063.
Hou et al., 1991, "Calcium and Phosphorous Fluxes During Hemodialysis with Low Calcium Dialysate", American Journal of Kidney Diseases, vol. 18: 217-224.
Hsu et al., 1984, "Renal Phosphate Excretion in Spontaneously Hypertensive and Normotensive Wistar Kyoto rats", Kidney International, vol. 25: 789-795.
Goodman et al., May 18, 2000, "Coronary-Artery Calcification in Young Adults with End-Stage Renal Disease Who are Undergoing Dialysis", The New England Journal of Medicine, vol. 342:1478-1483.
Hsu, Chen Hsing, Apr. 1997, "Are We Mismanaging Calcium and Phosphate Metabolism in Renal Failure?", American Journal of Kidney Diseases, vol. 29(4): 641-649.
Kuroda, et al., 1995, "Effect of Iron as a New Type of Phosphate Binder in Hemodialysis Patients", Japan J Nephrol, vol. 37, 468-473.
The Merck Index, 1996, 12th Ed., Entries for Acetic, Citric, Fumaric, Isocitric, succinic, and tartaric acid, published by Merck Research Laboratories.
Princiotto et al., 1970, "Absorption of Oral Chelated Iron", Biochemical Medicine, vol. 3: 289-297.
U.S. Final Office Action, Jun. 13, 2008, for Kwok et al., U.S. Appl. No. 11/206,981, filed Aug. 18, 2005.
U.S. Notice of Allowances and Fee(s) Due, Oct. 5, 2009, for Kwok et al., U.S. Appl. No. 11/206,981, filed Aug. 18, 2005.

(56) References Cited

OTHER PUBLICATIONS

European Office Communication for GloboAsia, et al., European Application No. EP 04712312.0, filed Sep. 19, 2005, Dated Feb. 18, 2009.
Australian Examiner's First Report, May 8, 2009 for Australian App'l No. 2004213819, filed Aug. 23, 2005.
Chinese Pre-Exam Results for Hsiao et al., Nov. 21, 2003, Chinese Application No. 03157490.4, filed Sep. 22, 2003. (w/English Translation).
Chinese Notification for Completion of Formalities for Registration, Dec. 5, 2007, for GloboAsia, LLC, Chinese Publication No. CN 1751056A, filed Mar. 22, 2006.
Eurasian Notification on the Necessity of Presenting Additional Materials, Jul. 3, 2009, for Eurasian App'l No. 200800593/28, filed Mar. 18, 2008.
European Office Communication, Aug. 4, 2009, for European App'l No. 04712312.0, filed Sep. 13, 2005.
Indian First Examination Report, Mar. 12, 2009, for Indian App'l No. 944/MUMNP/2005, filed Aug. 24, 2005.
Australian Notice of Acceptance, Aug. 18, 2009 for Australian App'l No. 2004213819, filed Aug. 23, 2005.
Israeli Office Action for GloboAsia, LLC, et al., Feb. 8, 2009, Israeli Application No. 170382, filed Aug. 18, 2005. (w/English translation).
Israeli Office Action, Aug. 17, 2009, for Israeli Application No. IL 170382, filed Aug. 18, 2005.
Israeli Preliminary Office Action, Sep. 3, 2009, for Israeli App'l No. IL 189583, filed Aug. 18, 2006.
Israeli Preliminary Office Action, Nov. 15, 2009, for Israeli App'l No. IL 192545, filed Jun. 30, 2008.
Moore, C.V., 1968, Entry for "Iron", in Modern Nutrition in Health and Disease, Michael G. Wohl and Robert S. Goodhart Eds., Published by Lea & Febiger, Philadelphia.
Naveh-Many et al., 1995, "Parathyroid Cell Mitoses in Normal and Chronic Renal Failure Rats: The Effects of Calcium, Phosphate, and Vitamin D", American Society of Nephrology, vol. 6: 968.
Niecestro et al., 2006, "A Phase II, Randomized, Double-Blind, Placebo-Controlled, Dose-Ranging Study of Ferric Citrate (FC) on Serum Phosphorous Levels in ESRD Patients." (Abstract only).
Niecestro et al., 2006, "Ferric Citrate (Phosphate Binder): Effects on Serum Iron and Other Parameters in ESRD Patients." (Abstract only).
Niecestro Robert, 2007, "Ferric Citrate for the Treatment of Hyperphosphatemia in ESRD" Abstract of article to be filed.
Niecestro et al., 2007, "A Randomized, Double-Blind, Placebo-Controlled Dose Ranging Study of the Effects of Ferric Citrate on Serum Phosphorus in Patients with End Stage Renal Disease (ESRD)", Article to be published.
Niecestro et al., "A Randomized, Double-Blind, Placebo-Controlled, Dose-Ranging Study of the Effects of Ferric Citrate on Serum Phosphorous Levels in Patients with End Stage Renal Disease (ESRD)." (PowerPoint Presentation).
Niecestro et al., "Ferric Citrate for the Treatment of Hyperphosphatemia in ESRD." (Abstract only).
Piraino et al., 1992, "Calcium Mass Transfer in Peritoneal Dialysis Patients Using 2.5 mEg/l Calcium Dialysate", Clinical Nephrology, vol. 37: 48-51.
Portale et al., 1989, "Effect of Dietary Phosphorous on Circulating Concentrations of 1,25-Dihydroxyvitamin D and Immunoreactive Parathyroid Hormone in Children with Moderate Renal Insufficiency", Journal of Clinical Investigation, vol. 73: 1580-1589.
Israeli Office Action, Sep. 14, 2010, for Israeli Application No. IL 193099, filed Jul. 28, 2008.
Israeli Office Action, Sep. 5, 2010, for Israeli Application No. IL 192545, filed Jun. 30, 2008.
Japanese Office Action, Dec. 16, 2010, for Japanese Application No. JP 2007-133978, filed May 21, 2007.
Mexico Office Action, Sep. 7, 2010, for Mexican Application No. PA/a/2005/008784, filed Aug. 18, 2005.
Mexico Office Action, Oct. 4, 2010, for Mexican Application No. MX/A/2008/002360, filed Aug. 18, 2005.
U.S. Office Action, Jul. 27, 2010, for Chan et al., U.S. Appl. No. 12/162,543, filed Jul. 29, 2008.
U.S. Office Action, Nov. 24, 2010, for Chan et al., U.S. Appl. No. 12/162,543, filed Jul. 29, 2008.
U.S. Office Action, Jan. 12, 2011, for Chan et al., U.S. Appl. No. 12/162,558, filed Jul. 29, 2008.
Chinese Office Action, Jan. 27, 2011, for GloboAsia LLC, Chinese Application No. 200680032108.2, Filed Feb. 29, 2008.
Chinese First Office Action, Jun. 9, 2011, for GloboAsia LLC, Chinese Application No. 200780003990.2, Filed Jun. 29, 2008.
Moe, et al., 2004, "Pathophysiology of Vascular Calcification in Chronic Kidney Disease" Circulation Research, Journal of the American Heart Association, 560-567.
Tonelli, et al., 2010, "Oral Phosphate Binders in Patients with Kidney Failure" New Engl J Med, 362: 1312-1324.
Australian Examination Report, Jun. 20, 2011, for GloboAsia LLC, Australian Application No. 2006279333, Filed Mar. 14, 2008.
Eurasian Office Action, Jun. 27, 2011, for GloboAsia LLC, Eaurasian Application No. 200800593, Filed Mar. 18, 2008.
Israeli Office Action, Jul. 10, 2011, for GloboAsia LLC, Israeli Application No. 189583, Filed Feb. 18, 2008.
Mexican Office Action, May 27, 2011, for GloboAsia LLC, Mexican Application No. MX/A/2008/002360, Filed Feb. 18, 2008.
Philipine Office Action, Jul. 20, 2011, for GloboAsia LLC, Philippines App'l No. 1-2005-501521, Filed Aug. 19, 2005.
Australian Examination Report, Dec. 20, 2011, for GloboAsia LLC, Australian Application No. 2006279333, Filed Mar. 14, 2008.
Australian Examination Report, Mar. 28, 2012, for GloboAsia LLC, Australian Application No. 2006279333, Filed Mar. 14, 2008.
Canadian Office Action, Jan. 31, 2012, for GloboAsia LLC, Canadian Patent No. 2,516,471, Filed Aug. 18, 2005.
Canadian Office Action, Jul. 9, 2013, for GloboAsia LLC, Canadian Application No. 2,640,974, Filed Jul. 30, 2008. [Exhibit 3].
Chinese Office Action, Aug. 30, 2012, for GloboAsia LLC, Chinese Application No. 200780003990.2, Filed Jul. 30, 2008. [Exhibit 4].
Chinese Office Action, Aug. 31, 2012, for GloboAsia LLC, Chinese Application No. 200780003983.2, Filed Jul. 30, 2008. [Exhibit 5].
Eurasian Notification of Readiness to Grant, Oct. 30, 2012, for Eurasian Application No. 200800593, filed Mar. 18, 2008. [Exhibit 6].
European Office Action, Dec. 3, 2012, for GloboAsia, LLC, European Application No. EP 04712312.0, filed Sep. 19, 2005. [Exhibit 7].
European Office Action, Dec. 20, 2012, for GloboAsia LLC, European Application No. EP11155958.9, Filed Feb. 25, 2011. [Exhibit 8].
European Office Action, Feb. 1, 2013, for GloboAsia LLC, European Application No. EP 07762833.7, Filed Jun. 29, 2008. [Exhibit 9].
European Office Action, Apr. 12, 2013, for GloboAsia LLC, European Application No. 07717051.2, Filed Jun. 29, 2008 . [Exhibit 10].
Israeli Office Action, Jul. 4, 2012, for GloboAsia LLC, Israeli Application No. IL 192545, filed Jun. 30, 2008. [Exhibit 11].
Israeli Office Action, Jul. 15, 2012, for GloboAsia LLC, Israeli Application No. IL 193099, filed Jul. 28, 2008. [Exhibit 12].
Hsu et al., 1990, "Factors Influencing Calcitriol Metabolism in Renal Failure", Kidney International, vol. 37: 44-50.
Hsu et al., 1999, "New Phosphate Binding Agents: Ferric Compounds", Journal of the American Society of Nephrology, vol. 10:1274-1280.
Jacobs, A., and Miles, P.M., 1969, "Role of gastric secretion in iron absorption," Gut 10:226-229.
Japan, 1999, "Japan's Specifications and Standard for Food Additives", vol. 7: D205-208, D376-382, D428-430, D552-554, D936-938, D1030-1032, D1425-1428. (English translation will be provided at a later date).
Karlinsky et al., 1980, "Preservation of Renal Function in Experimental Glomerulonephritis", Kidney International, vol. 17: 293-302.
Kawatetsu Techno Res. KK, 2003, "Manufacture of Ferric Ammonia Citrate, for Supplying Iron Ions in Chemical Reaction, Involves Adding Ammonia Gas and/or Aqueous Ammonia to Iron Citrate", WPIDS (abstract only).
Kilav et al., 1995, "Parathyroid Hormone Gene Expression in Hypophosphatemic Rats", Journal of Clinical Investigation, vol. 96: 327-333.

(56) References Cited

OTHER PUBLICATIONS

King, Earl Judson, 1939, "The Biochemistry of Silicic Acid: The Determination of Silica", The Biochemical Journal, vol. 33(6):944-954.
King, Earl Judson, and McGeroge, Murray, 1938, "The Biochemistry of Silicic Acid: The Solution and Excretion of Silica", The Biochemical Journal, vol. 32(2):426-433.
Kuroda et al., 1995, "Effect of Iron as a New Type of Phosphate Binder in Hemodialysis Patients" Chemical Abstracts Ann., 82815.
U.S. Appl. No. 60/447,690, filed Feb. 19, 2003, Kwok, et al.
U.S. Appl. No. 60/462,684, filed Apr. 15, 2003, Kwok, et al.
U.S. Appl. No. 60/709,511, filed Aug. 19, 2005, Kwok, et al.
U.S. Appl. No. 12/064,058, filed Feb. 18, 2008, Chan, et al.
U.S. Appl. No. 12/162,558, filed Jul. 29, 2008, Chan et al.
U.S. Appl. No. 12/162,543, filed Oct. 29, 2008, Chan et al.
Chinese Notification for the Grant of Invention Patent Rights for GloboAsia, LLC, Chinese App'l No. 200480004726.7, filed Aug. 19, 2005, Dated Nov. 16, 2007.
Chinese Office Action for GloboAsia, LLC, Chinese Application No. 03157490.4, filed Sep. 22, 2003, Dated Aug. 12, 2005.
Supplementary Partial European Search Report for Chen Hsing Hsu, European Application No. 97948333.6, filed Nov. 14, 1997, Dated Jan. 28, 2002.
European Office Communication for Chen Hsing Hsu, European Application No. 97948333.6, filed Nov. 14, 1997, Dated Jun. 16, 2003.
European Office Communication for Chen Hsing Hsu, European Application No. 97948333.6, filed Nov. 14, 1997, Dated May 16, 2006.
European Communication, for Chen Hsing Hsu, European Application No. 97948333.6, filed Nov. 14, 1997, Dated May 16, 2007.
European Communication under Rule 71(3) EPC for Chen Hsing Hsu, European App'l No. 97948333.6, filed Nov. 14, 1997, Dated Jan. 21, 2008.
Supplementary European Search Report for Globoasia, LLC, European Application No. EP 04712312.0, filed Sep. 19, 2005, Dated Apr. 28, 2008.
Eurasian Conclusion on Patentability of the Invention for GloboAsia, LLC, Eurasian App'l No. 200501322, filed Sep. 19, 2005, Dated Mar. 26, 2007.
Eurasian Notification of Readiness to Grant a Eurasian Patent for GloboAsia, LLC, Eurasian Application No. 200501322, filed Sep. 19, 2005, Dated Oct. 26, 2007.
Norwegian Office Action for Chen Hsing Hsu, Norwegian Application No. 19992936, filed Jun. 16, 1999, Dated Jan. 15, 2007.
Norwegian Office Action for Chen Hsing Hsu, Norwegian Application No. 19992936, filed Jun. 16, 1999, Dated Oct. 17, 2007.
Thailand Office Action for GloboAsia, LLC, Thailand Application No. 0601003938, filed Aug. 17, 2006, Dated Nov. 15, 2007.
Vietnam Office Action for GloboAsia, LLC, Vietnam Application No. 1-2005-01292, filed Sep. 16, 2005, Dated Jan. 9, 2008.
U.S. Office Action for Hsiao et al., U.S. Appl. No. 10/682,045, filed Oct. 8, 2003, Dated Jun. 1, 2004.
U.S. Office Action for Hsiao et al., U.S. Appl. No. 10/682,045, filed Oct. 8, 2003, Dated Sep. 22, 2004.
U.S. Notice of Allowance and Fee(s) Due for Hsiao et al., U.S. Appl. No. 10/682,045, filed Oct. 8, 2003, Dated Jan. 26, 2005.
U.S. Office Action for Chen Hsing Hsu, U.S. Appl. No. 08/794,328, filed Feb. 3, 1997, Dated Jul. 7, 1997.
U.S. Notice of Allowance and Fee(s) Due for Chen Hsing Hsu, U.S. Appl. No. 08/794,328, filed Feb. 3, 1997, Dated Jan. 7, 1998.
Sika et al., 2009, "Evaluation of Ferric Citrate as a Phosphate Binder in Dialysis Patients Requiring High Doses of Phosphate Binder", Zerenex Poster presented at the American Society of Nephrology Conference, Oct. 2009.
U.S. Office Action, Feb. 26, 2009, for Kwok et al., U.S. Appl. No. 11/206,981, filed Aug. 18, 2005.
Japanese Office Action, Mar. 16, 2010, for GloboAsia, LLC, Japanese App'l No. 2006-503637, Filed Aug. 18, 2005.
Mexican Office Action, Feb. 23, 2010, for GloboAsia, LLC, Mexican App'l No. PA/A/2005/008784, Filed Aug. 18, 2005.
New Zealand Office Action, Mar. 29, 2010, for GloboAsia, LLC, New Zealand App'l No. 566743, Filed Mar. 17, 2008.
In-Pharma Technologist.com, Jun. 8, 2005, "Pharma-grade ferric citrate patented", Sep. 17, 2008, http://www.in-pharmatechnologist.com/Materials-Formulation/Pharma-grade-ferric-citrate-patented.
The Ferric Citrate Study Group, 2006, "A Phase II Randomized, Double-Blind, Placebo-Controlled, Dose-Ranging Study of Ferric Citrate (FC) on Serum Phosphorous Levels" Abstract of Patent application to be filed.
Canadian Office Action, Aug. 30, 2010, for Canadian Application No. 2,516,471, Filed Aug. 18, 2005.
European Office Action, Nov. 10, 2010, for GloboAsia LLC, European Application No. 04712312.0, Filed Sep. 13, 2005.
European Extended Search Report, Jan. 12, 2011, for GloboAsia LLC, European Application No. 06813544.1, Filed Mar. 18, 2008.
Japanese Final Rejection, May 24, 2011, for GloboAsia LLC, Japanese Application No. JP 2006-503637, Filed Aug. 18, 2005.
Korean Office Action, Feb. 7, 2011, for GloboAsia LLC, Korean Application No. 10-2005-7014976, Filed Aug. 12, 2005.
Mexican Office Action, Mar. 29, 2011, for GloboAsia LLC, Mexican Application No. PA/A/2005/008784, Filed Aug. 18, 2005.
Taiwanese Office Action, Jul. 27, 2010, for GloboAsia, LLC, Taiwanese Application No. 093103743, filed Feb. 17, 2004.
U.S. Office Action, Jun. 7, 2011, for Chan et al., U.S. Appl. No. 12/162,558, filed Jul. 29, 2008.
Chertow, et al., 2002, "Sevelamer attenuates the progression of coronary and aortic calcification in hemodialysis patients", Kidney International, vol. 62: 245-252.
Cozzolino, et al., 2001, "Role of Calcium-Phosphate Product and Bone-Associated Proteins on Vascular Calcification in Renal Failure" J Am Soc Nephrol 12: 2511-2516.
Giachelli, 2009, "The Emerging Role of Phosphate in Vascular Calcification" Kidney International, 75(9): 890-897.
London, et al., 2000, "Calcification of the Aortic Valve in the Dialyzed Patient", J Am Soc Nephrol 11: 778-783.
Chinese Office Action, Apr. 13, 2012, for GloboAsia LLC, Chinese Application No. 200780003990.2, Filed Jul. 30, 2008.
Chinese Office Action, Dec. 31, 2011, for GloboAsia LLC, Chinese Application No. 200680032108.2, Filed Feb. 29, 2008.
Chinese Office Action, Dec. 7, 2011, for GloboAsia LLC, Chinese Application No. 200780003983.2, Filed Jul. 30, 2008.
Chinese Rejection Decision, May 3, 2012, for GloboAsia LLC, Chinese Application No. 200680032108.2, Filed Feb. 29, 2008.
Eurasian Office Action, Mar. 22, 2012 for Eurasian Application No. 200800593, Filed Mar. 8, 2008.
European Search Report, Mar. 12, 2012, for GloboAsia LLC, European Application No. EP11155958.9, Filed Feb. 25, 2011.
European Search Report, Apr. 16, 2012, for GloboAsia LLC, European Application No. EP07762833.7, Filed Jun. 29, 2008.
European Search Report, Apr. 18, 2012, for GloboAsia LLC, European Application No. EP07717051.2, Filed Jun. 29, 2008.
Indian Examination Report, Jan. 23, 2012, for GloboAsia LLC, Indian Application No. 1414/MUMNP/2008, Filed Jul. 7, 2008.
Indian Examination Report, Jan. 17, 2012, for GloboAsia LLC, Indian Application No. 1413/MUMNP/2008, Filed Jul. 7, 2008.
Israeli Office Action, Dec. 19, 2011, for GloboAsia LLC, Israeli Application No. 189583, Filed Feb. 18, 2008.
Japanese Final Office Action, Nov. 15, 2011, for GloboAsia LLC, Japanese Application No. 2006-503637, Filed Aug. 18, 2005.
Japanese Office Action, Mar. 13, 2012, for GloboAsia LLC, Japanese Application No. 2008-527177, Filed Feb. 18, 2008.
Taiwanese Office Action, May 1, 2012, for GloboAsia LLC, Taiwanese Application No. 95130373, Filed Aug. 18, 2006.
U.S. Office Action, Jan. 17, 2012, for GloboAsia LLC, U.S. Appl. No. 12/711,679, filed Feb. 24, 2010.
U.S. Office Action, Mar. 21, 2012, for GloboAsia LLC, U.S. Appl. No. 12/711,679, filed Feb. 24, 2010.
U.S. Final Office Action, Jan. 4, 2012, for GloboAsia LLC, U.S. Appl. No. 12/162,543, filed Jul. 29, 2008.
U.S. Final Office Action, Dec. 7, 2011, for GloboAsia LLC, U.S. Appl. No. 12/162,558, filed Jul. 29, 2008.

(56) References Cited

OTHER PUBLICATIONS

PCT International Search Report, Nov. 25, 2010, for Henry Trong Le, International App'l No. PCT/US2010/042788, Filed Jul. 21, 2010.
PCT Written Opinion, Jan. 21, 2012, for Henry Trong Le, International App'l No. PCT/US2010/042788, Filed Jul. 21, 2010.
Israeli Office Action, Aug. 12, 2012, for Israeli Application No. IL 189583, filed Aug. 18, 2006. [Exhibit 13].
Israeli Office Action, Feb. 19, 2013, for Israeli Application No. IL 189583, filed Aug. 18, 2006. [Exhibit 14].
Japanese Office Action, Jan. 8, 2013, for GloboAsia LLC, Japanese Application No. 2008-552435, Filed Jul. 30, 2008. [Exhibit 15].
Japanese Office Action, Jan. 8, 2013, for GloboAsia LLC, Japanese Application No. 2008-552431, Filed Jul. 30, 2008. [Exhibit 16].
Japanese Final Rejection, Jan. 15, 2013, for GloboAsia LLC, Japanese Application No. 2008-527177, Filed Feb. 18, 2008. [Exhibit 17].
Japanese Office Action, Jun. 25, 2013, for GloboAsia LLC, Japanese Application No. 2008-527177, Filed Feb. 18, 2008. [Exhibit 18].
Mexican Office Action, Jul. 2, 2013, for GloboAsia LLC, Mexican Application No. MX/A/2011/000585, Filed Jan. 14, 2011. [Exhibit 19].
U.S. Office Action, Sep. 7, 2012, for GloboAsia LLC, U.S. Appl. No. 12/162,543, filed Jul. 29, 2008. [Exhibit 20].
U.S. Office Action, Jan. 9, 2013, for GloboAsia, LLC for U.S. Appl. No. 12/162,558, filed Jul. 29, 2008. [Exhibit 21].
U.S. Office Action, May 8, 2012, for GloboAsia LLC, U.S. Appl. No. 13/289,048, filed Nov. 4, 2011. [Exhibit 22].
Korean Office Action, Dec. 17, 2012, for GloboAsia LLC, Korean Application No. 10-2008-7018633, Filed Jul. 29, 2008.
Korean Office Action, Jun. 28, 2013, for GloboAsia LLC, Korean Application No. 10-2008-7018633, Filed Jul. 29, 2008.
U.S. Final Office Action, Sep. 5, 2013, for GloboAsia, LLC for U.S. Appl. No. 12/162,558, filed Jul. 29, 2008.
Bernacca et al., "Chemical modification of bovine pericardium and its effect on calcification in the rat subdermal model." Biomaterials. 1992; vol. 13(6):345-52.
Australian Office Action, Feb. 5, 2013, for GloboAsia LLC, Australian Application No. 2007210096, Filed Jul. 2, 2008.
Australian Office Action, Feb. 25, 2013, for GloboAsia LLC, Australian Application No. 2007210090, Filed Jul. 2, 2008.
Australian Office Action, Mar. 27, 2013, for GloboAsia LLC, Australian Application No. 2007210096, Filed Jul. 2, 2008.
Australian Office Action, May 20, 2013, for GloboAsia LLC, Australian Application No. 2007210096, Filed Jul. 2, 2008.
Australian Office Action, Apr. 24, 2013, for GloboAsia LLC, Australian Application No. 2007210090, Filed Jul. 2, 2008.
Chinese Office Action, Mar. 18, 2013, for GloboAsia LLC, Chinese Application No. 200780003983.2, Filed Jul. 30, 2008.
Chinese Office Action, Mar. 18, 2013, for GloboAsia LLC, Chinese Application No. 200780003990.2, Filed Jul. 30, 2008.
Korean Office Action, Jun. 28, 2013, for GloboAsia LLC, Korean Application No. 10-2008-7018634, Filed Jul. 29, 2008.
Korean Office Action, Dec. 17, 2012, for GloboAsia LLC, Korean Application No. 10-2008-7018634, Filed Jul. 29, 2008.
Korean Office Action, Feb. 8, 2013, for GloboAsia LLC, Korean Application No. 10-2008-7006131, Filed Mar. 13, 2008.
Kuroda et al., 1995, "Effect of Iron as a New Type of Phosphate Binder in Hemodialysis Patients", Japan J. Nephrol., vol. 37, 468-473.
Lakshmanan et al., 1984, "Calcium and Phosphorus Intakes, Balances, and Blood Levels of Adults Consuming Self-selected Diets", American Journal of Clinical Nutrition, vol. 40: 1368-1379.
Lau, Kai, 1989, "Phosphate Excess and Progressive Renal Failure: The Precipitation-Calcification Hypothesis", Kidney International, vol. 36: 918-937.
Lau et al., 1990, "Fluids and Electrolytes", W.B. Saunders Company, Second Edition, Philadelphia, Ch. 8: 505-571.
Liu et al., 1943, "Studies of Calcium and Phosphorous Metabolism with Special Reference to Pathogenesis and Effects of Dihydrotachysterol (A.T.10) and Iron", Medicine, vol. 22: 103-161.
Lopez-Hilker et al., 1990, "Phosphorous Restriction Reverses Hyperparathyroidism in Uremia Independent of Changes in Calcium and Calcitriol", American Journal of Physiology, vol. 259: F432-437.
Lumlertgul et al., 1986, "Phosphate Depletion Arrests Progression of Chronic Renal Failure Independent of Protein Intake", Kidney International, vol. 29: 658-666.
Martis et al., 1989, "Calcium Cabonate as a Phosphate Binder: Is There a Need to Adjust Peritoneal Dialysate Calcium Concentrations for Patients Using CaCO3?", Peritoneal Dialysis International, vol. 9 325-328.
Matkovic et al., 1992, "Calcium Balance during Human Growth: Evidence for Threshold Behavior", American Journal of Clinical Nutrition, vol. 55: 992-996.
Meyer et al., 1982, "Trace Metal-Citric Acid Complexes as Inhibitors of Calcification and Crystal Growth. I. Effects of Fe(III), Cr(III), and Ai(III) Complexes on Calcium Phosphate Crystal Growth", J Urol, vol. 128, No. 6, 1372-1375.
Korean Final Office Action, Sep. 29, 2011, for GloboAsia LLC, Korean Application No. 10-2005-7014976, Filed Aug. 12, 2005.
U.S. Office Action, Mar. 8, 2011, for Chan et al., U.S. Appl. No. 12/064,058, filed Feb. 18, 2008.
U.S. Office Action, Oct. 22, 2010, for Chan et al., U.S. Appl. No. 12/064,058, filed Feb. 18, 2008.
Japanese Office Action, Jul. 31, 2012, for GloboAsia LLC, Japanese Application No. 2008-552435, Filed Jul. 30, 2008.
Japanese Office Action, Jul. 31, 2012, for GloboAsia LLC, Japanese Application No. 2008-552431, Filed Jul. 30, 2008.
European Office Action, Jun. 13, 2012, for GloboAsia LLC, European Application No. EP06813544.1, Filed Mar. 18, 2008.
European Office Action, May 9, 2012, for GloboAsia LLC, European Application No. EP 04712312.0, Filed Sep. 13, 2005.
European Office Action, May 7, 2012, for GloboAsia LLC, European Application No. EP07717051.2, Filed Jun. 29, 2008.
Canadian Office Action, Mar. 5, 2013, for GloboAsia LLC, Canadian Application No. 2.640,763, Filed Jul. 30, 2008. [Exhibit 1].
Canadian Office Examination Report, Oct. 15, 2012, for GloboAsia LLC, Canadian Application No. 2,619,591, Filed Feb. 15, 2008. [Exhibit 2].
PCT International Search Report for GloboAsia, LLC, et al., International Application No. PCT/US2006/032385, filed Aug. 18, 2006, Dated Mar. 2, 2007.
PCT Written Opinion of the International Searching Authority for GloboAsia, LLC, et al., International Application No. PCT/US2006/032385, filed Aug. 18, 2006, Dated Mar. 2, 2007.
Rivet, et al., 2006, "Cutaneous Calcification in Patients With End-Stage Renal Disease", Arch. Dermatol., vol. 142: 900-906.
Yang, et al., 2002, "An Open-Label, Crossover Study of a New Phosphate-Binding Agent in Haemodialysis Patients: Ferric Citrate", Nephrology Dialysis Transplantation, vol. 17: 265-270.
PCT International Search Report for GloboAsia, LLC et al., International Application No. PCT/US2004/004646, filed Feb. 18, 2004, Dated Jan. 26, 2005.
PCT Written Opinion of the International Searching Authority for GloboAsia, LLC et al., International Application No. PCT/US2004/004646, filed Feb. 18, 2004, Dated Jan. 26, 2005.
PCT International Preliminary Report on Patentability for GloboAsia, LLC et al., International Application No. PCT/US2004/004646, filed Feb. 18, 2004, Dated Aug. 19, 2005.
PCT International Preliminary Report on Patentability for GloboAsia, LLC et al., International Application No. PCT/US2006/032385, filed Aug. 18, 2006, Dated Feb. 28, 2008.
PCT International Search Report for GloboAsia, LLC et al., International Application No. PCT/US2007/002157, filed Jan. 26, 2007, Dated Dec. 5, 2007.
PCT Written Opinion of the International Searching Authority for GloboAsia, LLC et al., International Application No. PCT/US2007/002157, filed Jan. 26, 2007, Dated Dec. 5, 2007.

\* cited by examiner

Pharmaceutical-Grade Ferric Citrate Manufacture Flow Chart

Figure 9

Summary of Clinical Results

Efficacy End Points

| Baseline | Linear Regression<br>Dose Response | Change from<br>Each Dose vs Placebo |
|---|---|---|
| Serum $PO_4$ (mg/dL) | | |
| Day 14 | No (p=0.0523) | No |
| Day 28 | Yes (p=0.073) | Yes (6g/day, p=0.0119) |
| Serum $Ca*PO_4$ $(mg/dL)^2$ | | |
| Day 14 | No (p=0.0401) | No |
| Day 28 | Yes (p=0.158) | Yes (6g/day, p=0.0378) |
| | | |
| Serum Ca (mg/dL), Days 14&28 | No | No |
| Serum Iron (mg/dL), Days 14&28 | No | No |
| Serum Ferritin (mg/dL), Days 14&28 | No | No |
| Transferrin Saturation %, Days 14&28 | No | No |
| Total IBCs, Days 14&28 | No | No |

Figure 10

Summary- Efficacy End Points

|  | Placebo (N=16) | 2 g/day (N=31) | 4 g/day (N=32) | 6 g/day (N=32) | Dose Response |
|---|---|---|---|---|---|
| Serum [PO4] (mg/dL) at Day 0 | 7.2±1.43 | 7.2±1.23 | 7.1±1.27 | 7.3±1.33 | N/A |
| Serum [PO4] (mg/dL) at Day 14 | 6.7±1.22 | 6.7±1.50 | 6.4±1.56 | 6.3±1.72 | No (P=0.0523) |
| Serum [PO4] (mg/dL) at Day 28 | 7.2±1.45 | 6.9±2.22 | 6.0±1.33 | 5.8±1.76* | Yes |

|  | Placebo (N=16) | 2 g/day (N=31) | 4 g/day (N=32) | 6 g/day (N=32) | Dose Response |
|---|---|---|---|---|---|
| $[Ca]*[PO4]\ (mg/dL)^2$ at Day 0 | 62.8±13.91 | 62.8±13.92 | 63.5±10.69 | 65.8±12.19 | N/A |
| $[Ca]*[PO4]\ (mg/dL)^2$ at Day 14 | 59.9±12.19 | 60.3±16.50 | 59.9±13.89 | 57.5±16.27 | Yes |
| $[Ca]*[PO4]\ (mg/dL)^2$ at Day 28 | 63.2±12.55 | 61.7±21.25 | 55.4±13.36 | 54.1±17.68* | Yes |

*P<0.05, Significant Difference Baseline Change as Compared to Placebo

Figure 11

Summary- Safety Data

|  | Placebo (N=16) # Event (%) | 2 g/day (N=33) # Event (%) | 4 g/day (N=34) # Event (%) | 6 g/day (N=33) # Event (%) |
|---|---|---|---|---|
| Total number of subjects with at least one adverse event (T#at1AE) | 7 (43.8) | 16 (48.5) | 12 (35.3) | 17 (51.5) |
| Sorted by Prefered Term (PT) | | | | |
| Abdominal Pain | 0 (0.0) | 0 (0.0) | 4 (11.8) | 2 (6.1) |
| Diarrhea | 2 (12.5) | 3 (9.1) | 1 (2.9) | 1 (3.0) |
| Sorted by System Organ Class/PT | | | | |
| GI Disorders (see above PT) | 4 (25.0) | 8 (24.2) | 10 (29.4) | 10 (30.3) |
| General Disorders | 2 (12.5) | 4 (12.1) | 2 (5.9) | 4 (12.1) |
| Infections and Infestations | 2 (12.5) | 0 (0.0) | 3 (8.8) | 1 (3.0) |
| Skin and SC Tissue Disorders | 0 (0.0) | 3 (9.1) | 0 (0.0) | 4 (12.1) |
| Sorted by SOC/PT/Severity | | | | |
| T#at1AE, Mild | 7 (43.8) | 13 (39.4) | 9 (26.5) | 14 (42.4) |
| T#at1AE, Moderate | 0 (0.0) | 6 (18.2) | 3 (8.8) | 2 (6.1) |
| T#at1AE, Severe | 1 (6.3) | 0 (0.0) | 0 (0.0) | 4 (12.1) |
| GI Disorders, Mild | 4 (25.0) | 6 (18.2) | 8 (23.5) | 9 (27.3) |
| Sorted by SOC/PT/Relationship | | | | |
| T#at1AE, Definitely | 0 (0.0) | 0 (0.0) | 0 (0.0) | 0 (0.0) |
| T#at1AE, Probably | 1 (6.3) | 2 (6.1) | 2 (5.9) | 5 (15.2) |
| T#at1AE, Possibly | 3 (18.8) | 5 (15.2) | 6 (17.6) | 2 (6.1) |
| GI Disorders, Definitely | 0 (0.0) | 0 (0.0) | 0 (0.0) | 0 (0.0) |
| GI Disorders, Probably | 1 (6.3) | 2 (6.1) | 2 (5.9) | 5 (15.2) |
| GI Disorders, Possibly | 3 (18.8) | 3 (9.1) | 6 (17.6) | 1 (3.0) |

Figure 12

Safety Profile Comparison Between Chemical Grade And Pharmaceutical Grade Ferric Citrate

| | Placebo (N=16) | | Pharmaceutical grade Ferric Citrate Phase II Clinical Study 2005 | | | | | | Chemical grade Ferric Citrate Clinical Study in Taiwan 1998 | | Chemical grade Ferric Citrate Clinical Study in U.S 1998 | |
|---|---|---|---|---|---|---|---|---|---|---|---|---|
| | | | Ferric Citrate 2g/day (N=33) | | Ferric Citrate 4g/day (N=34) | | Ferric Citrate 6g/day (N=33) | | Ferric Citrate 3g/day (N=45) | | Ferric Citrate 4.5g/day (N=14) | |
| | # Event | % | # Event | % | # Event | % | # Event | % | # Event | % | # Event | % |
| Diarrhea | 2 | 12.5% | 3 | 9.1% | 1 | 2.9% | 1 | 3.0% | 9 | 20.0% | 3 | 21.4% |
| Loose stool | 1 | 6.3% | 0 | 0.0% | 1 | 2.9% | 1 | 3.0% | 3 | 6.7% | 5 | 35.7% |
| Constipation | 0 | 0.0% | 0 | 0.0% | 2 | 5.9% | 1 | 3.0% | 4 | 8.9% | 1 | 7.1% |
| Bloating | 1 | 6.3% | 0 | 0.0% | 0 | 0.0% | 1 | 3.0% | 5 | 11.1% | 3 | 21.4% |
| Nausea | 0 | 0.0% | 2 | 6.1% | 0 | 0.0% | 1 | 3.0% | 0 | 0.0% | 0 | 0.0% |

Conclusions: (1) The safety profile of the pharmaceutical grade appears to be much better than the chemical grade.
(2) There are no difference in safety profile between the placebo group and the 3 treatment groups (2, 4, and 6 g/day) in the pharmaceutical grade Phase II Clinical Study.

Figure 13

Efficacy comparison between chemical grade and pharmaceutical grade studies

Serum phosphorus (mg/dl)

| | Pharmaceutical grade Ferric Citrate Clinical Study 2005 | | | | Chemical grade Ferric Citrate Clinical Study in Taiwan 1998 | | Chemical grade Ferric Citrate Clinical Study in U.S 1998 | |
|---|---|---|---|---|---|---|---|---|
| | Placebo | Ferric Citrate 2g/day (N=33) | Ferric Citrate 4g/day (N=34) | Ferric Citrate 6g/day (N=33) | Ferric Citrate 3g/day (N=45) | Ferric Citrate 6g/day (N=33) | Ferric Citrate 3g/day (N=45) | Ferric Citrate 4.5g/day (N=14) |
| Day 0 (Baseline) | 7.2±1.4 | 7.2±1.2 | 7.1±1.3 | 7.3±1.3 | 6.7±1.9 | | 7.2±2.5 | |
| Day 28 (End of treatment) | 7.2±1.2 | 6.9±2.2 | 6.0±1.3 | 5.8±1.8 | 5.7±1.6 | | 5.9±2.0 | |
| Difference from baseline | -0.1±2.0 | -0.3±2.1 | -1.1±1.6 | -1.5±1.6 | -1.0±2.5 | | -1.3±3.2 | |

$[Ca]\times[P]$ (mg/dl)$^2$

| | Pharmaceutical grade Ferric Citrate Clinical Study 2005 | | | | Chemical grade Ferric Citrate Clinical Study in Taiwan 1998 | Chemical grade Ferric Citrate Clinical Study in U.S 1998 |
|---|---|---|---|---|---|---|
| | Placebo | Ferric Citrate 2g/day (N=33) | Ferric Citrate 4g/day (N=34) | Ferric Citrate 6g/day (N=33) | Ferric Citrate 3g/day (N=45) | Ferric Citrate 4.5g/day (N=14) |
| Day 0 (Baseline) | 62.8±14.0 | 62.9±13.3 | 63.5±10.7 | 65.8±12.2 | 60.8±17.1 | 60.3±15.5 |
| Day 28 (End of treatment) | 63.2±12.6 | 61.7±21.3 | 55.4±13.4 | 54.1±17.7 | 51.8±15.2 | 51.8±17.7 |
| Difference from baseline | -0.3±19.3 | -1.1±20.7 | -8.1±14.7 | -11.7±15.4 | -9.0±22.9 | -8.5±23.5 |

Conclusions: Both efficacy parameters (serum phosphate level and [Ca]x[P] level) exhibit dose-related decrease.

ial-grade ferric organic compounds, such as ferric
PHARMACEUTICAL-GRADE FERRIC ORGANIC COMPOUNDS, USES THEREOF AND METHODS OF MAKING SAME This application is a Continuation of U.S. Ser. No. 13/289,048, filed Nov. 4, 2011 (now allowed), which is a Continuation of U.S. Ser. No. 12/064,058, filed Feb. 18, 2008 (now U.S. Pat. No. 8,093,423), which is a National Stage of International Application No. PCT/US2006/032385, filed Aug. 18, 2006, which claims benefit of U.S. Ser. No. 60/709,511, filed Aug. 19, 2005, and U.S. Ser. No. 11/206,981, filed Aug. 18, 2005 (now U.S. Pat. No. 7,767,851), which is a Continuation-In-Part of Int'l App'l No. PCT/US2004/004646, filed Feb. 18, 2004, which claims benefit of U.S. Ser. No. 60/462,684, filed Apr. 15, 2003, and U.S. Ser. No. 60/447,690, filed Feb. 19, 2003. The entire contents and disclosures of the preceding applications are incorporated herein by reference into this application.

Throughout this application, various publications are referenced. Disclosures of these publications in their entireties are hereby incorporated by reference into this application to more fully describe the state of the art to which this invention pertains.

TECHNICAL FIELD

This invention relates to the preparation and use of pharmaceutical-grade ferric organic compounds, such as ferric citrate. Uses of the pharmaceutical-grade ferric citrate described herein, include, but are not limited to methods of treating various disorders in humans and non-human subjects or patients.

BACKGROUND OF THE INVENTION

Uses of Iron Compounds

Ferric iron containing compounds are useful in the treatment of a number of disorders, including, but not limited to, hyperphosphatemia and metabolic acidosis. See Hsu et al., "New Phosphate Binding Agents: Ferric Compounds", J Am Soc Nephrol, Vol. 10, Pages 1274-1280, 1999. Previous studies and inventions have reported the use of ferric compounds in binding with dietary phosphates, and such ferric compounds are potentially useful for the treatment of hyperphosphatemia in renal failure patients (U.S. Pat. No. 5,753,706, 1993; U.S. Pat. No. 6,903,235, 2005; CN 1315174, 2001; Yang W. C., et al., Nephrol. Dial. Transplant 17:265:270 (2002)). Elevated amounts of phosphate in the blood can be removed by administering compounds such as ferric citrate. Once in solution, the ferric iron binds phosphate, and the ferric phosphate compounds precipitate in the gastrointestinal tract, resulting in effective removal of dietary phosphate from the body. It is also believed that the absorbed citrate from ferric citrate is converted to bicarbonate which corrects metabolic acidosis, a condition common in renal failure patients.

Int'l App. No. PCT/US2004/004646, filed Feb. 18, 2004, published under Int'l Publication No, WO2004/074444 on Sep. 2, 2004, discloses a method of preparing ferric organic compounds, including ferric citrate that remains soluble over a wider range of pH than previously described preparations, and which have a large active surface area. However, commercially scalable manufacturing processes with quality control/analysis measures to ensure and/or to verify the compliance of the pharmaceutical-grade ferric citrate or ferric organic compounds with established standards or specifications were not previously disclosed.

Accordingly, there exists a need for a scalable process for synthesizing pharmaceutical-grade ferric organic compounds or ferric citrate for human use. The process needs to consistently produce ferric organic compounds or ferric citrate of the required pharmaceutical grade.

This invention further discloses dosage for ferric citrate for treating of a human or non-human subject or patient. in need of the compound. Different routes of administration are explored.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

An embodiment of the invention provides a manufacturing and quality control process/analysis for making a pharmaceutical-grade ferric citrate that consistently complies with the established Manufacture Release Specification. The process of the present invention can be adapted to produce multi-kilogram batches of pharmaceutical-grade ferric citrate, and can be readily scaled up to provide additional manufacturing capacity for ferric citrate.

An illustrative embodiment of the manufacturing method may be exemplified by the following non-limiting sequence of steps for preparing pharmaceutical-grade ferric citrate comprising the steps of (a) dissolving an appropriate amount of Ferric chloride hexahydrate in water to form a Ferric chloride hexahydrate solution; (b) dissolving an appropriate amount of NaOH in water to form a NaOH solution; (c) mixing the Ferric chloride hexahydrate solution and NaOH solution to form a solution with $Fe(OH)_3$ precipitate; (d) maintaining the pH of the solution with $Fe(OH)_3$ precipitate above 7.0; (e) isolating the $Fe(OH)_3$ precipitate; (f) washing the $Fe(OH)_3$ precipitate three times with water; (g) suspending the $Fe(OH)_3$ precipitate in water; (h) adding citric acid to the $Fe(OH)_3$ precipitate so form a ferric-organic acid solution; (i) stirring and heating the ferric-organic acid solution at 90-100° C. for 30 to 120 minutes; (j) removing solids in the ferric-organic acid solution by adding citric acid; (k) allowing the ferric-organic acid solution to cool to below 30° C.; (l) maintaining the pH of the ferric-organic acid solution to between 0.8-1.5; (m) filtering the ferric-organic acid solution to obtain a liquid filtrate; (n) mixing acetone and liquid filtrate to form ferric citrate; (o) isolating ferric citrate; (p) washing ferric citrate with acetone three times; and (q) drying the ferric citrate.

A further embodiment provides a large-scale production scheme for pharmaceutical-grade ferric citrate comprising the steps of: (a) mixing an appropriate amount of NaOH and Ferric chloride hexahydrate in a suitable reactor to form a ferric hydroxide slurry with ferric hydroxide precipitate; (b) maintaining the pH of the ferric hydroxide slurry to above 7.0; (c) isolating the ferric hydroxide precipitate from the ferric hydroxide slurry using pressure filtration; (d) washing the ferric hydroxide precipitate three times; (e) maintaining the % Cl in the ferric hydroxide precipitate to below 5%; (f) isolating the washed ferric hydroxide precipitate using pressure filtration; (g) mixing citric acid with washed ferric hydroxide precipitate to form a ferric organic acid solution; (h) stirring and maintaining the temperature of the ferric organic acid solution at 80±5° C. for 2 hours; (i) allowing the ferric organic acid solution to cool to 60° C.; (j) maintaining the pH of the ferric organic acid solution to between 0.8 to 1.5 and the amount of Fe in the ferric organic acid solution to ≥85% of Fe added in step (a); (k) filtering the ferric organic acid solution using pressure filtration to obtain a liquid filtrate; (l) mixing the liquid filtrate with acetone to obtain ferric citrate; (m) isolating ferric citrate using pressure filtration; (n) washing the ferric citrate with acetone; (o) isolating the washed ferric citrate using pressure filtration; (p) drying the washed ferric citrate in fluidized bed dryer; and (q) maintaining the organic volatile impurities to ≤1000 ppm acetone.

A further embodiment encompasses various intermediate compositions that may be useful in the preparation of the pharmaceutical-grade ferric citrate. The intermediate compositions encompassed herein include solids, liquids or multiphase mixtures. A liquid intermediate composition comprising the pharmaceutical-grade ferric citrate may be an aqueous composition or an organic solvent-based composition. A multiphase composition may encompass both aqueous and organic phases.

An additional embodiment encompasses the methods of storing, packaging and using the various intermediate compositions disclosed herein.

An additional embodiment provides pharmaceutically useful compositions comprising the pharmaceutical-grade ferric citrate. The pharmaceutically useful composition further comprises any pharmaceutically acceptable carrier, adjuvant, filler or delivery vehicle suitable for administering to a subject or human patient, an effective amount of the pharmaceutical-grade ferric citrate.

Further embodiments of the pharmaceutical compositions include, but are not limited to solids, liquids, or semi-solid forms, such as gels, syrups, chewables or pastes. Within the scope of the methods using the pharmaceutically useful compositions disclosed herein are effective doses of the pharmaceutical compositions, in addition to the timing and modes of administering the pharmaceutical compositions.

A non-limiting example a method for using the pharmaceutical compositions encompasses treating disorders resulting from elevated blood levels of phosphates, i.e., hyperphosphatemia, in a subject or a human patient. Such disorders are exemplified by, but not limited to, renal failure or the progression of renal failure, mineralization of soft tissues, hyperparathyroidism as well as other complications.

An embodiment encompassed by the invention includes a pharmaceutical composition comprising:
(a) an amount of a pharmaceutical-grade ferric organic compound effective to achieve a decrease in the serum phosphate level of a subject or patient;
(b) a pharmaceutically suitable carrier; and
wherein the ferric organic compound complies with at least one of the limits in the manufacture release specification in table A.

The pharmaceutical composition described herein may be prepared by a method shown in FIG. 1, 2, 3 or 4. Further to these embodiments are compositions prepared with materials satisfying at least one limit disclosed in each of the release specifications of either of the relevant Tables B to F.

An additional embodiment encompasses compositions of pharmaceutical-grade ferric citrate, prepared according to methods comprising the steps of:
   (a) dissolving an appropriate amount of ferric chloride hexahydrate in water to form a ferric chloride hexahydrate solution;
   (b) dissolving an appropriate amount of NaOH in water to form a NaOH solution;
   (c) mixing the ferric chloride hexahydrate solution and NaOH solution to form a solution with Fe(OH)3 precipitate;
   (d) maintaining the pH of the solution with $Fe(OH)_3$ precipitate above 7.0;
   (e) isolating the $Fe(OH)_3$ precipitate;
   (f) washing the $Fe(OH)_3$ precipitate three times with water;
   (g) suspending the $Fe(OH)_3$ precipitate in water;
   (h) adding citric acid to the $Fe(OH)_3$ precipitate to form a ferric-organic acid solution;
   (i) stirring and heating the ferric-organic acid solution at 90-100° C. for 30 to 120 minutes;
   (j) removing solids in the ferric-organic acid solution by adding citric acid;
   (k) allowing the ferric-organic acid solution to cool to below 30° C.;
   (l) maintaining the pH of the ferric-organic acid solution to between 0.8-1.5;
   (m) filtering the ferric-organic acid solution to obtain a liquid filtrate;
   (n) mixing acetone and liquid filtrate to form ferric citrate;
   (o) isolating ferric citrate;
   (p) washing ferric citrate with acetone three times;
   (q) drying the ferric citrate; and
   (r) performing quality control tests as shown in FIG. 1, 2 or 3.

It is advantageous to scale-up the method of preparation. Thus, an industrial-scale method is embodied by a method for large-scale production of pharmaceutical-grade ferric citrate comprising the steps of:
   (a) mixing an appropriate amount of NaOH and Ferric chloride hexahydrate in a suitable reactor to form a ferric hydroxide slurry with ferric hydroxide precipitate;
   (b) maintaining the pH of the ferric hydroxide slurry to above 7.0;
   (c) isolating the ferric hydroxide precipitate from the ferric hydroxide slurry using pressure filtration;
   (d) washing the ferric hydroxide precipitate three times;
   (e) maintaining the % Cl in the ferric hydroxide precipitate to below 5%;
   (f) isolating the washed ferric hydroxide precipitate using pressure filtration;
   (g) mixing citric acid with washed ferric hydroxide precipitate to form a ferric organic acid solution;
   (h) stirring and maintaining the temperature of the ferric organic acid solution at 80±5° C. for 2 hours;
   (i) allowing the ferric organic acid solution to cool to 60° C.;
   (j) maintaining the pH of the ferric organic acid solution to between 0.8 to 1.5 and the amount of Fe in the ferric organic acid solution to ≥85% of Fe added in step (a);
   (k) filtering the ferric organic acid solution using pressure filtration to obtain a liquid filtrate;
   (l) mixing the liquid filtrate with acetone to obtain ferric citrate;
   (m) isolating ferric citrate using pressure filtration;
   (n) washing the ferric citrate with acetone;
   (o) isolating the washed ferric citrate using pressure filtration;
   (p) drying the washed ferric citrate in fluidized bed dryer; and
   (q) maintaining the organic volatile impurities to ≤1000 ppm acetone;
and wherein the ferric citrate complies with at least one of the limits in the manufacture release specification in Table A.

The compositions encompassing pharmaceutical grade citrate are suitable for treating hyperphosphatemia, or other disorders characterized by high serum phosphate levels. Therefore, the invention encompasses treating subjects or patients with various renal diseases; e.g., End Stage Renal Diseases (ESRD), Chronic Kidney Disease (CKD) or other relate kidney diseases, or subjects and patients who are on dialysis but not limited to hemodialysis.

In another embodiment, the compositions encompassing pharmaceutical grade ferric citrate may used to treat subjects or patients with metabolic acidosis. Other disorders that may be ameliorated by the conversion of citrate to bicarbonate are also encompassed by the invention described.

An embodiment of a method for using the pharmaceutical composition encompasses treating a human or non-human subject or patient with chronic kidney disease. There are generally five clinical stages of chronic kidney disease, numbered 1 to 5, wherein stage 1 is the least severe and stage 5 the most severe. In the early stages, e.g., stages 1 and 2, dialysis is not required. As chronic kidney disease progresses to stage 5, a patient may require dialysis treatment three times per week. It should be noted that elevated phosphate levels are observed at all stages of chronic kidney disease. Therefore, an embodiment of the invention is a method of treating a subject or person with early or mid-stage chronic kidney disease, with a composition comprising pharmaceutical-grade ferric citrate in order to achieve a lower serum phosphate level.

It is a further embodiment of the invention to provide a method of treating a human or non-human subject or patient with late-stage chronic kidney disease who undergo hemodialysis, by administering a composition comprising pharmaceutical-grade ferric citrate. It is known that hemodialysis is not sufficiently effective in reducing serum phosphate level. The treatment of a subject or person with late stage kidney disease is applicable whether or not the subject or person is currently undergoing hemodialysis treatment.

An additional embodiment of the invention is a method of treating a subject or person with chronic kidney disease and undergoing peritoneal dialysis with the pharmaceutical-grade ferric citrate-containing compositions described. It is known that peritoneal dialysis is not sufficiently effective in reducing serum phosphate levels.

An additional embodiment is a method for using the pharmaceutical composition to inhibit or even reverse soft tissue mineralization, specifically calcification. Hyperphosphatemia may lead to increased calcium phosphate deposition in hard and soft tissues by increasing the likelihood of binding with free calcium to form insoluble calcium phosphate. Therefore, an effective dose of a composition comprising pharmaceutical-grade ferric citrate may decrease serum phosphate levels and result in a corresponding decrease in calcium phosphate deposition.

It is noteworthy that whereas ferric ion forms insoluble precipitates with phosphate-containing compounds in the lumen of the gastroinstestinal tract, the citrate component is absorbed and functions as a calcium chelator. Because chelated calcium is not available for calcium phosphate formation, administering pharmaceutical-grade ferric citrate decreases may lead to reductions in both serum calcium and phosphate. This may also be expressed as leading to a decrease in the serum calcium-phosphate product. Reducing serum calcium and phosphate would be expected to reduce calcium phosphate deposition. The end result is reversing, i.e., solubilizing or dissolving, the deposited calcium phosphate.

The decalcifying of a calcified soft tissue, e.g., the sclera of the eye, may be achieved by administering pharmaceutical-grade ferric citrate. It is known among persons of ordinary skill in the relevant medical arts that patients with kidney disease receiving doses of ferric citrate have shown reversal of calcium deposits on the eye. Therefore, an embodiment of the invention is directed to the decalcification of soft tissue such as the eye.

Kidney stones comprise calcium salts of oxalic acid or phosphates and are formed by mechanisms similar to those described above. Thus, pharmaceutical-grade ferric citrate, in another embodiment of the invention provides a method of treating kidney stones, i.e., renal calculi, by promoting their dissolution.

The compositions encompassing pharmaceutical grade ferric citrate may operate according to more than one mechanism. A plausible non-limiting mechanism of action may result from the ferric ion binding phosphate in the GI tract, thus forming an insoluble ferric phosphate precipitate. This, in turn, may result in decrease the uptake of phosphate and phosphate-containing compounds from the GI tract.

In view of such a mechanism, the administering of compositions encompassing pharmaceutical grade ferric citrate via an oral route is encompassed by the inventive methods described.

This invention provides a method of reversing, preventing or stabilizing soft tissue calcification of a subject, comprising administering to said subject and effective amount of a ferric citrate compound.

This invention further provides a method of reversing, preventing or stabilizing soft tissue calcification of a subject, comprising administering to said subject and effective amount of a ferric citrate compound, wherein the ferric citrate compound is prepared according to a method as shown in FIGS. 1-4.

This invention provides a method of reversing, preventing or stabilizing soft tissue calcification of a subject, comprising administering to said subject and effective amount of a ferric citrate compound, wherein the ferric citrate compound is prepared according a method comprising the steps of:

An embodiment of the invention encompasses tolerable doses of up to 15 grams per day for ferric citrate capsules and 30 grams per day for ferric citrate tablets.

The compositions encompassing pharmaceutical grade ferric citrate may be administered for varying periods of time. In some embodiments, the tolerability of the compositions encompassing pharmaceutical grade ferric citrate allows for long term administration when necessary.

DETAILED DESCRIPTION OF THE FIGURES

In drawings which illustrate specific embodiments of the invention, but which should not be construed as restricting the spirit or scope of the invention in any way:

Figure 14:
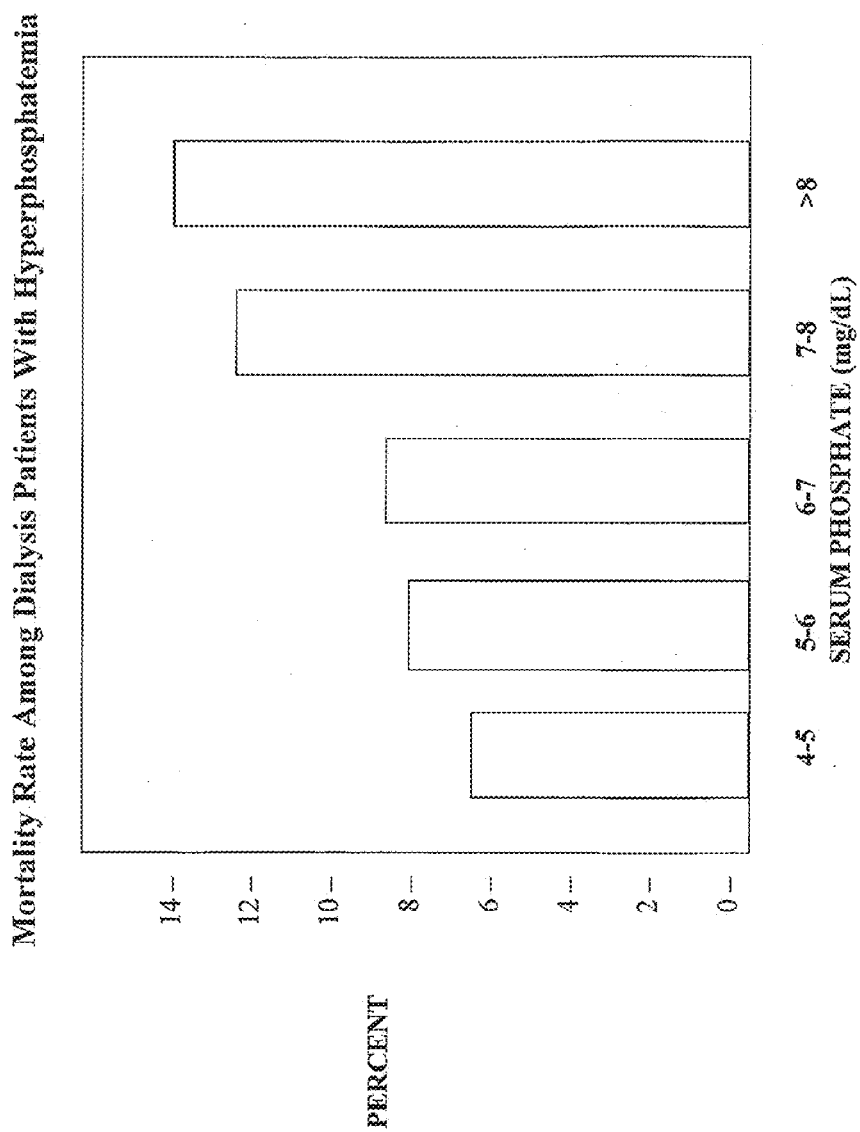

FIG. 9 is a summary of clinical results for pharmaceutical-grade ferric citrate FIG. 10 is a summary of the efficacy data for pharmaceutical-grade ferric citrate FIG. 11 is a summary of the safety data from a clinical study FIG. 12 is a comparison of the safety profiles of chemical grade and pharmaceutical grade ferric citrates FIG. 13 is a comparison of the efficacy profiles of chemical grade and pharmaceutical grade ferric citrates FIG. 14 shows a bar graph of the relationship between the rate of dialysis patient mortality and hyperphosphatemia

DETAILED DESCRIPTION OF THE INVENTION

In drawings which illustrate specific embodiments of the invention, but which should not be construed as restricting the spirit or described in detail to avoid unnecessarily obscuring the invention. Accordingly, the specification and drawings are to be regarded in an illustrative, rather than a restrictive, sense.

Throughout this application, references are made to the United States Pharmacopeia (USP), and the latest edition of the USP, USP 28, is hereby incorporated by reference into this application in its entirety.

This invention provides a method of preparing pharmaceutical-grade ferric citrate, comprising the steps of: (a) dissolving an appropriate amount of Ferric chloride hexahydrate in water to form a Ferric chloride hexahydrate solution; (b) dissolving an appropriate amount of NaOH in water to form a NaOH solution; (c) mixing the Ferric chloride hexahydrate solution and NaOH solution to form a solution with $Fe(OH)_3$ precipitate; (d) maintaining the pH of the solution with $Fe(OH)_3$ precipitate above 7.0; (e) isolating the $Fe(OH)_3$ precipitate; (f) washing the $Fe(OH)_3$ precipitate three times with water; (g) suspending the $Fe(OH)_3$ precipitate in water; (h) adding citric acid to the $Fe(OH)_3$ precipitate to form a ferric-organic acid solution; (i) stirring and heating the ferric-organic acid solution at 90-100° C. for 30 to 120 minutes; (j) removing solids in the ferric-organic acid solution by adding citric acid; (k) allowing the ferric-organic acid solution to cool no below 30° C.; (l) maintaining the pH of the ferric-organic acid solution to between 0.8-1.5; (m) filtering the ferric organic acid solution to obtain a liquid filtrate; (n) mixing acetone and liquid filtrate to form ferric citrate; (o) isolating ferric citrate; (p) washing ferric citrate with acetone three times; and (q) drying the ferric citrate.

This invention provides a method for scalable or large-scale production of pharmaceutical-grade ferric citrate comprising the steps of (a) mixing an appropriate amount of NaOH and Ferric chloride hexahydrate in a suitable reactor so form a ferric hydroxide slurry with ferric hydroxide precipitate; (b) maintaining she pH of the ferric hydroxide slurry to above 7.0; (c) isolating the ferric hydroxide precipitate from the ferric hydroxide slurry using pressure filtration; (d) washing the ferric hydroxide precipitate three times; (e) maintaining the % Cl in the ferric hydroxide precipitate to below 5%; (f) isolating the washed ferric hydroxide precipitate using pressure filtration; (g) mixing citric acid with washed ferric hydroxide precipitate to form a ferric organic acid solution; (h) stirring and maintaining the temperature of the ferric organic acid solution at 80±5° C. for 2 hours; (i) allowing the ferric organic acid solution to cool to 60° C.; (j) maintaining the pH of the ferric organic acid solution to between 0.8 to 1.5 and the amount of Fe in the ferric organic acid solution to ≥85% of Fe added in step (a); (k) filtering the ferric organic acid solution using pressure filtration to obtain a liquid filtrate; (l) mixing the liquid filtrate with acetone to obtain ferric citrate; (m) isolating ferric citrate using pressure filtration; (n) washing the ferric citrate with acetone; (o) isolating the washed ferric citrate using pressure filtration; (p) drying the washed ferric citrate in fluidized bed dryer; and (q) maintaining the organic volatile impurities to ≤1000 ppm acetone.

In an embodiment, the ferric chloride hexahydrate complies with the release specification as shown in Table B; the citric acid complies with the release specification as shown in Table F; the water complies with she release specification as shown in Table D; the acetone complies with the release specification as shown in Table E; and the sodium hydroxide complies with the release specification as shown in Table C.

In another embodiment, she ferric citrate is dried using a fluidized bed dryer or is dried under vacuum.

In a further embodiment, the process as described above further comprises testing the ferric citrate for compliance with the release specification as shown in Table A. In a further embodiment, testing comprises performing at least one test selected from the group consisting of: assay content purity of ferric citrate and ferric citrate monohydrate; assay content of citric acid; assay content of detectable ferric citrate related substances; assay content of ferric ion; elemental iron impurity test; limit of ferrous iron test; loss on drying test; hydrate test (water content by differential scanning calorimetry); hydrate test (water content by karl Fischer Titration); trace or heavy metals test (As, Ca, Cd, Cu, Fe, Hg, Na, Pb, Sr, Zn); limit of oxalic acid test; identification A for ferric salts test; identification B by FTIR test; insoluble substances test; limit of ammonium test; limit of chloride test; limit of nitrate test; limit of tartrate test; residue on ignition test; organic volatile impurities test; and microbial, mold and yeast test.

This invention provides a pharmaceutical-grade ferric citrate prepared according to the methods described above.

This invention provides a composition comprising the ferric citrate prepared according to the methods described above for treating hyperphosphatemia or metabolic acidosis.

This invention provides a composition prepared according to the methods described above for treating disorders responsive to ferric organic compound therapy.

Figure 6:
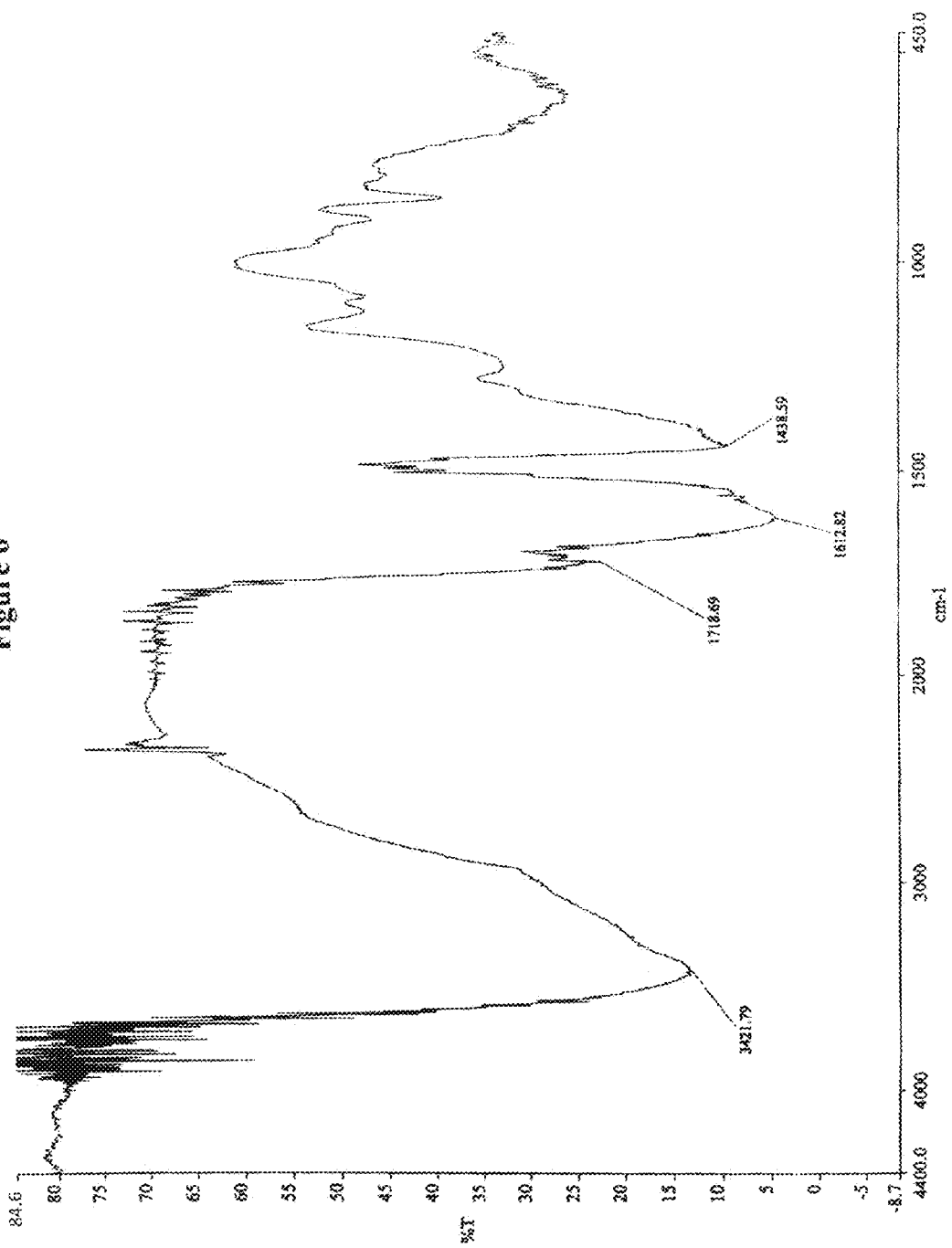
FIG. 6 shows the representative FTIR spectrum for pharmaceutical-grade ferric citrate according to the invention.

This invention provides a pharmaceutical-grade ferric citrate prepared according to the methods described above, wherein the ferric citrate produces the peak as shown in FIG. 6 when subjected to NMR spectroscopy analysis.

Figure 8:
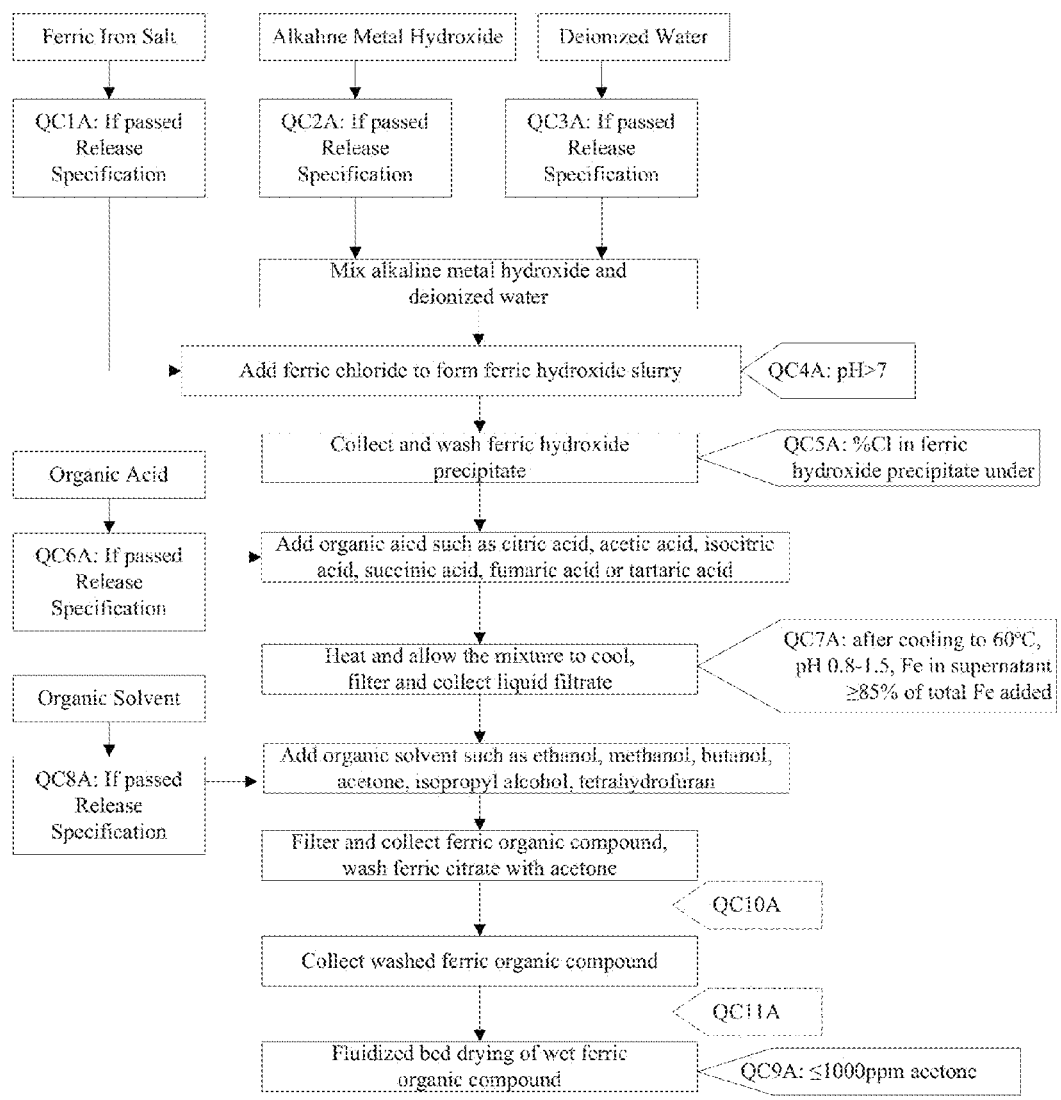
FIG. 8 is a schematic diagram outlining the general method for synthesis of pharmaceutical-grade ferric organic compound including in-process quality control measures to ensure the final ferric organic compound complies with established Manufacture Release Specification.

This invention provides a pharmaceutical-grade ferric citrate prepared according to the methods described above, wherein the ferric citrate possesses the dissolution rates as shown in FIG. 8.

Figure 7:
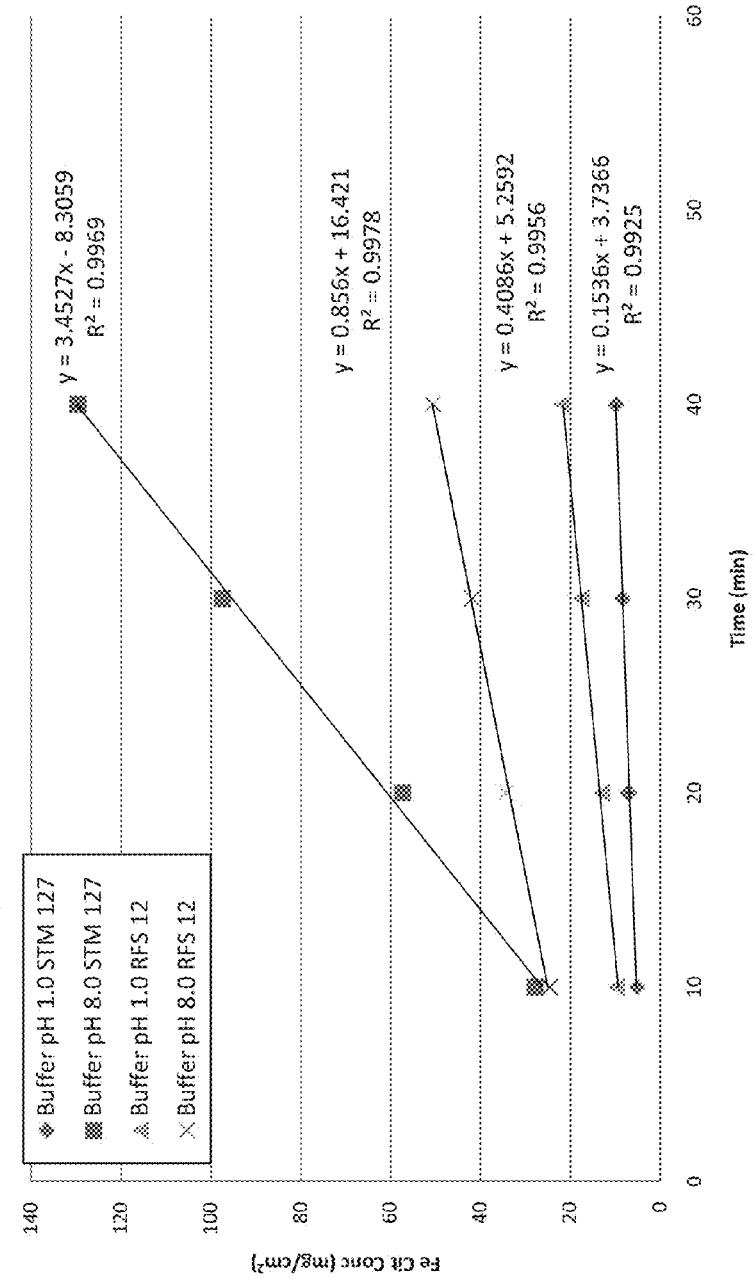
FIG. 7 is a comparison of intrinsic dissolution rates at pH 1.0 and 8.0 for pharmaceutical grade and chemical grade ferric citrate.

This invention provides a pharmaceutical-grade ferric citrate prepared according to the methods described above, wherein the ferric citrate produces the spectral data as shown in FIG. 7 when subjected to Fourier Transform Infrared Spectrometry (FTIR) spectrum analysis.

This invention provides a composition comprising the ferric citrate as described above for treating hyperphosphatemia or metabolic acidosis.

This invention provides a composition comprising the ferric acid as describe above for treating disorders responsive to ferric organic compound therapy.

This invention provides a pharmaceutical-grade ferric citrate prepared by the process comprising the steps as shown in FIG. 1-4.

The pharmaceutical-grade ferric citrate according no she invention is useful for treating a subject suffering from hyperphosphatemia, metabolic acidosis or a disorder responsive to ferric organic compound therapy. In an embodiment, the subject is a human being.

The invention also provide a use for a composition comprising pharmaceutical-grade ferric citrate effective for one or more of the following uses,
  (a) treating hyperphosphatemia;
  (b) decreasing mortality rate in dialysis patients;
  (c) treating metabolic acidosis;
  (d) inhibiting calcium phosphate deposition;
  (e) decreasing serum calcium-phosphate product ([Ca]×[P])
  (f) decreasing serum calcium levels;
  (g) reversing calcification of soft tissue; and
  (h) aiding to dissolve a kidney stone.

The use may further encompass at least partly relying on reducing serum levels of calcium and phosphate ions.

The uses as stated above may apply to soft tissue such as a blood vessel or an eye.

The uses as stated may be carried cut by administering over a long-term.

The invention allows for the above-stated uses to be achieved wherein the use is accompanied by less gastrointestinal adverse side effects than if the composition comprised chemical grade ferric citrate.

In accordance with the above-stated uses, the invention provides for a method for treating a disorder characterized by a high serum phosphate level comprising administering an effective amount of a composition comprising pharmaceutical-grade ferric citrate.

The invention also provides for the method wherein an effective amount of pharmaceutical-grade ferric citrate is administered in the form of a tablet, a powder, a suspension, an emulsion, a capsule, a lozenge, a granule, a troche, a pill, a liquid, a spirit, or a syrup.

The invention also provides for the method wherein the effective amount of pharmaceutical-grade ferric citrate is from 2 to 100 grams per day, preferably between 4 and 60 grams per day.

In some embodiments, the method may provide a daily effective amount of 2, 4, 6, or 8 grams, In general, hyperphosphatemia is prevalent in patients with chronic renal failure and in patients on dialysis. There is also evidence that indicate elevated serum phosphorus, calcium-phosphorus product (Ca×P) and parathyroid hormone (PTH) levels contribute to increased incidence of vascular, visceral, peripheral vascular and soft tissue calcification in renal disease patients Thus, it is an additional novel feature of the claimed invention to prevent or reverse calcification in renal disease patient or in a normal person. For example, dissolving kidney stones that may accompany renal failure.

Phosphorous exerts a negative impact on vascular calcification by direct participation in the Ca×P and indirectly in the pathogenesis and progression of hyperthyroidism. Serum calcium and phosphorous are metastable under normal circumstances, which means that their concentrations are not sufficient to produce spontaneous precipitation. However, once the calcification process begins, the concentrations are sufficient to support crystal proliferation.

Available evidence confirms a high prevalence of underlying vascular disease and structural heart disease in patients with severe chronic renal failure. These structural lesions are then exposed to elevated serum phosphorus, Ca×P, and PTH (1).

Factors which are considered likely to contribute to elevated serum phosphorus and Ca×P include administration of calcium-containing phosphorus binders. The calcium-containing phosphorus binders, such as calcium acetate are prescribed to many new hemodialysis (HD) and peritoneal dialysis (PD) patients, thus providing a large source of exogenous calcium to the GI tract.

Calcification also extends beyond renal disease patients and can include anyone who is over the age of 40. While the leading cause of death in the United States is acute myocardial infarction and stroke, hypercholesteromia contribute to only 15% of the deaths in this category and 85% is caused by ventricular calcification.

It has been shown that abnormalities in serum phosphorous, Ca×P and PTH levels can result in vascular, visceral and/or soft tissue calcification. For example, calcifications of myocardium, coronary arteries, cornea can lead to the development of a number of clinically significant complications including myocardial ischemia, myocardial infarction, impaired myocardial function, congestive heart failure, cardiac valve insufficiency and blindness.

Accordingly, there exists a need for methods of managing or reducing serum phosphorous as a means of treating numerous medical disorders. The method includes administering a phosphate binder which does not adversely affect serum calcium levels and does not cause toxic side effects in the patient.

EXAMPLES

In examples which are intended to illustrate embodiments of the invention but which are not intended to limit the scope of the invention:

Example 1

General Method for Synthesis of a Pharmaceutical-Grade Ferric Citrate

Figure 1:
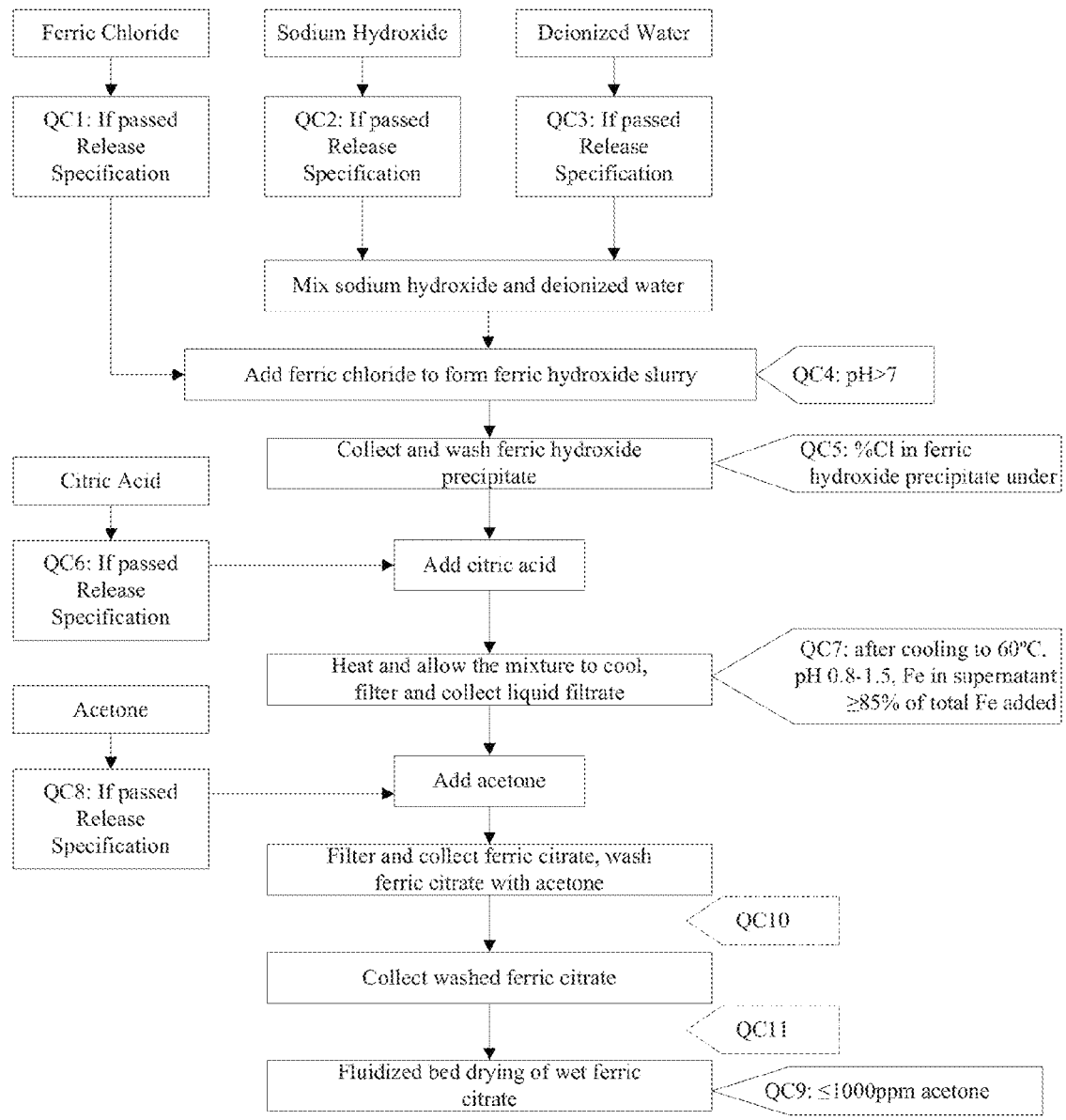
FIG. 1 is a schematic diagram outlining the general method for synthesis of pharmaceutical-grade ferric citrate including in-process quality control measures to ensure the final ferric citrate product complies with the established Manufacture Release Specification as shown in Table A.
Figure 2:
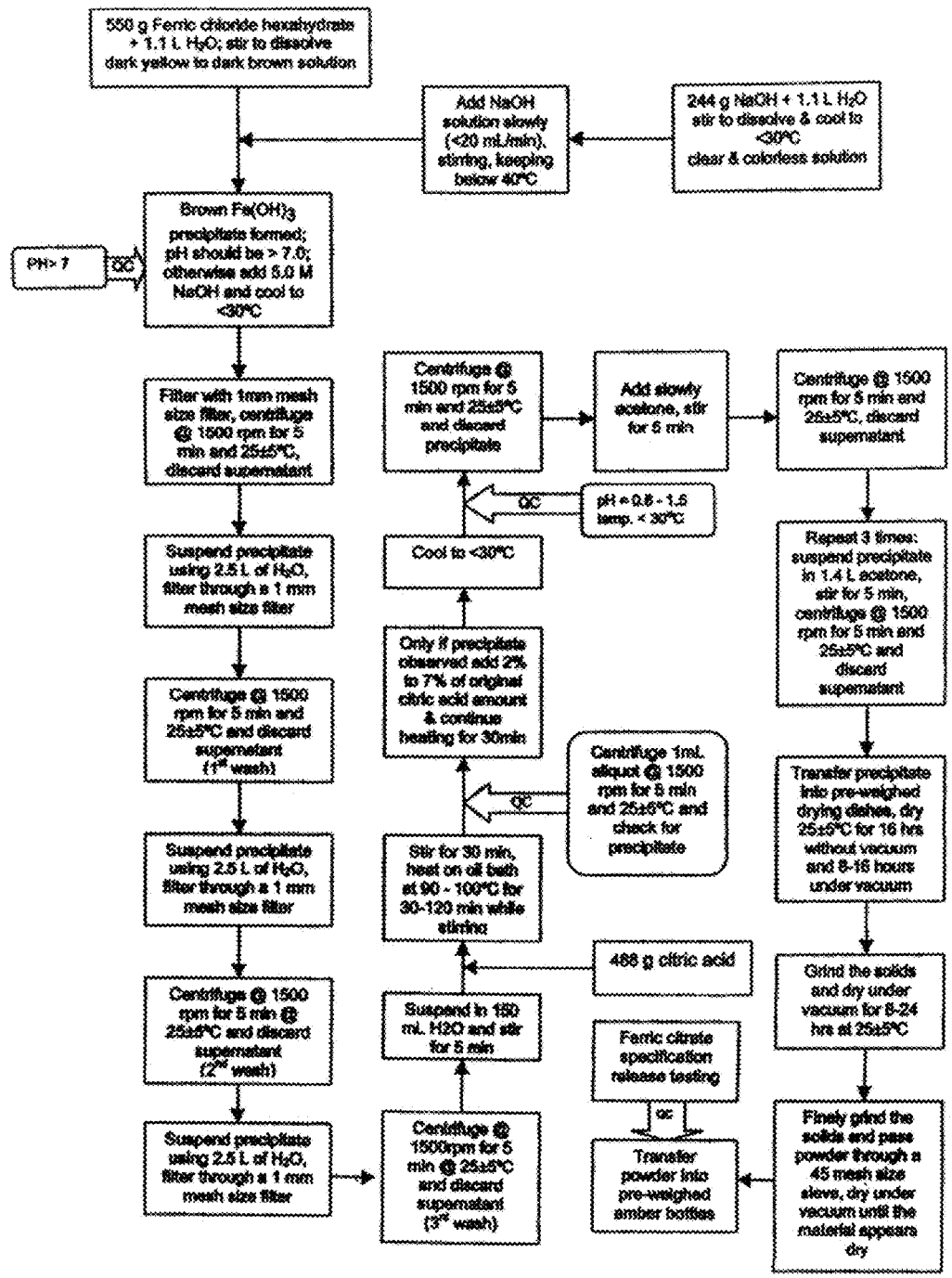
FIG. 2 is a schematic digram outlining a method of making pharmaceutical-grade ferric citrate according to the invention.

Referring to FIG. 1, which shows a general method of synthesis of the pharmaceutical-grade ferric citrate according to the invention, the flow chart shows implementation of quality control measures at selected stages of the synthesis process to ensure the final ferric citrate product complies with the Manufacture Release Specification as shown in Table A or any established Manufacture Release Specification for pharmaceutical-grade ferric citrate which have been approved or are suitable for human use. Other quality control measures or procedures, which are readily apparent to one of ordinary skill in the art, can be used or incorporated into the pharmaceutical-grade synthesis process to maintain the quality and purity of the final product and to increase the efficiency and yield of the synthesis process. See, for example, QC10 and QC11 in FIG. 1.

Examples of quality control measures employed in the synthesis process include: (QC4) maintaining pH of the ferric hydroxide slurry above 7.0; (QC5) maintaining the % Cl in ferric hydroxide precipitate below 5%; (QC7) maintaining the pH of the mixture between 0.8-1.5 and the Fe in mixture ≥85% of total Fe added after adding citric acid to ferric hydroxide precipitate; and (QC9) maintaining the level, of acetone to ≤1000 ppm during the drying stage.

In an embodiment, the raw materials, i.e., ferric chloride, deionized water, citric acid, acetone, sodium hydroxide, must pass release specifications, such as those provided on Table B-F, before they can be used in the synthesis process. See FIG. 1, QC1-QC3, QC6 and QC8.

Example 1A

General Method for Synthesis of a Pharmaceutical-Grade Ferric Organic Compounds

Referring to FIG. 10, which shows a general method of synthesis of the pharmaceutical-grade ferric organic compounds according to the invention, the flow chart shows implementation of quality control measures at selected stages of the synthesis process to ensure the final ferric citrate product complies with established Manufacture Release Specification for pharmaceutical-grade ferric organic compounds which have been approved or are suitable for human use. Other quality control measures or procedures, which are readily apparent to one of ordinary skill in the art, can be used or incorporated into the pharmaceutical-grade synthesis process to maintain the quality and purity of the final product and to increase the efficiency and yield of the synthesis process. See, for example, QC10A and QC11A in FIG. 10.

Examples of quality control measures employed in the synthesis process include: (QC4A) maintaining pH of the ferric hydroxide slurry above 7.0; (QC5A) maintaining the % Cl in ferric hydroxide precipitate below 5%; (QC7A) maintaining the pH of the mixture between 0.8-1.5 and the Fe in mixture ≥85% of total Fe added after adding organic acid to ferric hydroxide precipitate; and (QC9A) maintaining the level of organic solvent to ≤1000 ppm during the drying stage.

In an embodiment, the raw materials, i.e., ferric iron salt, deionized water, organic acid, organic solvent, alkaline metal hydroxide, must pass release specifications before they can be used in the synthesis process. See FIG. 1, QC1A-QC3A, QC6A and QC8A. The organic acid can comprise citric acid, acetic acid, isocitric acid, succinic acid, fumaric acid, tartaric acid, or any other suitable organic acid. The organic solvent can comprise ethanol, methanol, butanol, acetone, isopropyl alcohol, tetrahydrofuran, or any other suitable organic solvent.

Example 2

Solubility Profile of Ferric Organic Compounds According to the Invention

The ferric organic compounds produced according to the methods described above are more soluble than commercially available ferric organic compounds, over a wider range of pH levels. This increase in solubility of the ferric organic compounds of she present invention is believed to be a result of the unique significantly large active surface area of the ferric organic compounds of the present invention. For example, at pH 8.0, the intrinsic dissolution rate of ferric citrate of the present invention is 3.08 times greater than the commercially available ferric citrate. See Table 1.

The intrinsic dissolution rates of commercially available ferric citrate were compared with the ferric citrate of the present invention. The intrinsic dissolution rate is defined as the dissolution rate of pure substances under the condition of constant surface area. The dissolution rate and bioavailability of a drug substance is influence by its solid state properties: crystallinity, amorphism, polymorphism, hydration, solvation, particle size and particle surface area. The measured intrinsic dissolution rate is dependent on these solid-state properties and is typically determined by exposing a constant surface area of a material to an appropriate dissolution medium while maintaining constant temperature, stirring rate, and pH. The intrinsic dissolution rates are presented in Table 1.

TABLE 1

Intrinsic dissolution rates of ferric citrate at 37° C. in solutions of pH 8

| Sample | Rate of Acetone Addition (ml/min) | Intrinsic Dissolution Rates (mg/cm2/min) | Mean Intrinsic Dissolution Rates (mg/cm2/min) |
|---|---|---|---|
| RFS-12 (sigma/commercially available) | 10.0 | 0.83 | 0.83 |
| STM-134 (reference material) | 10.0 | 1.88 | 3.08 |
| PAN031203A (experimental batch 1) | 10.0 | 3.82 | |
| PAN031203B (experimental batch 2) | 10.0 | 4.00 | |
| PAN031203C (experimental batch 3) | 9.5 | 2.68 | |
| PAN031203D (experimental batch 4) | 40 | 2.95 | |
| PAN031203E (experimental batch 5) | 4.4 | 3.13 | |

For example, the BET active surface area of the ferric citrate of the present invention is at least 16 times larger than the commercially available ferric citrate. See Table 2.

The analysis of active surface area is based on BET theory which describes the phenomenon of mass and energy interaction and phase changes during as adsorption onto solid surfaces and in pore spaces. In BET active surface area measurement, the volume of a monolayer of gas is determined which allows the surface area of the sample to be determined using the area occupied by a single layer of adsorbed gas molecule. Table 4 is a comparison of the active surface area of the ferric citrate of the present invention compared to the active surface area of commercially available ferric citrate compounds.

TABLE 2

BET active surface areas of various forms of ferric citrate

| Sample | Mean Dissolution Rates (mg/cm2/min) | BET Active Surface Area |
|---|---|---|
| RFS-12-1 (sigma/commercially available) | 0.76 | 0.61 |
| RFS-12-2 (sigma/commercially available) | | |
| STM-134-1 (reference material 1) | 2.47 | 16.17 |
| STM-134-2 (reference material 2) | | |
| STM-182-1 (lab-scale 500 g batch 1) | 2.61 | 19.85 |
| STM-182-2 (lab-scale 500 g batch 2) | | |

Example 3

Use of Ferric Organic Compounds According to the Invention in the Treatment of Disorders The ferric organic compounds produced according to the methods described above are useful in the treatment of hyperphosphatemia, metabolic acidosis, and any other disorders responsive to ferric organic compound therapy. Because the ferric organic compounds of the present invention are more soluble than commercially available ferric organic compounds, smaller amounts of the ferric organic compounds of the present invention can be used to effectively treat patients suffering from such disorders.

Improved aqueous solubility is particularly relevant to the use of the ferric organic compounds of the present invention in the treatment of disorders responsive to ferric organic compound therapy. Because the ferric organic compounds of the present invention are more soluble, they will be more effective when taken orally, and therefore can be taken in lower doses. The ferric organic compounds of the present invention are more soluble over a wider pH range than commercially available ferric organic compounds; therefore, the ferric organic compounds of the present invention can be more effective by being soluble in the small intestine.

For example, in an experiment simulating the alkaline condition in the small intestine, the ferric citrate of the present invention showed better dissolution rate than the commercially available ferric citrate. It is suggested that the ferric citrate of the present invention can be more effective by being more soluble in the small intestine. See Table 1. As a result, patients can take lower doses of medication with lower incidences of side effects.

In one embodiment of the invention, the ferric citrate of the present invention has a significantly higher rate of aqueous solubility under physiological conditions than commercially available forms of ferric citrate, and therefore the ferric citrate of the present invention is believed to provide a significant improvement in the orally effective use of ferric citrate at a reduced dosage. By reducing the orally effective dose of ferric citrate, it is believed that the ferric citrate of the present invention will provide a lower incidence of ulcerative gastrointestinal adverse effects associated with commercially available ferric citrate compounds. In addition, it is believed that the increased rate of dissolution of the ferric citrate of the present invention will provide a more rapid onset of action in binding to dietary phosphate.

The ferric organic compounds of the present invention can be administered in a number of forms, including orally administrable forms, which can comprise the ferric organic compounds of the present invention alone or in combination with a pharmaceutically acceptable carrier. The orally administrable form includes, but is not limited to, a tablet, a powder, a suspension, an emulsion, a capsule, a granule, a troche, a pill, a liquid, a spirit, or a syrup. The composition can be administered to human beings or other animals suffering from illnesses responsive to ferric organic compound therapy.

Example 4

A Method of Making a Pharmaceutical-grade Ferric Citrate

The present invention describes a process for manufacturing pharmaceutical-grade ferric citrate suitable as an active pharmaceutical ingredient for human use. An overview of the Ferric Citrate Manufacture Flow Chart is shown in FIG. 1. For a specific example, pharmaceutical-grade ferric citrate was produced using the procedure described below. Also see FIG. 2.

4.1. Preparation of Ferric Chloride Solution
  Weigh 550 g of ferric chloride hexahydrate (correct for CoA purity) into a 1 L beaker.
  Transfer the ferric chloride hexahydrate into a 4 L Erlenmeyer flask.
  Measure 1.1 L of deionized water using a graduated cylinder. Use a small portion of the deionized water to rinse the beaker and transfer the water into the 4 L Erlenmeyer flask. Transfer the remaining water into the Erlenmeyer flask.
  Stir solution using a magnetic stirring bar until completely dissolved. The solution is a dark yellow to dark brown color.

4.2. Preparation of Sodium Hydroxide Solution
  Weigh 244 g of sodium hydroxide (correct for CoA purity) into a 500 mL beaker.
  Transfer the sodium hydroxide into a 2 L Erlenmeyer flask.
  Measure 1.1 L of deionized water using a graduated cylinder. Use a small portion of the deionized water to rinse the beaker and transfer the water into a 4 L Erlenmeyer flask. Transfer the remaining water into the Erlenmeyer flask slowly.
  In a fumehood, stir the solution using a stirring bar while adding she water and stir until completely dissolved. The solution is clear and colorless.
  Cool solution to below 30° C. using a water bath.

4.3. Preparation of Ferric Hydroxide Intermediate
  Place a magnetic stirring bar into the ferric chloride solution and place the flask in a water bath. Set up on a stirring plate and start the stirring plate at a low speed.
  Add slowly the sodium hydroxide solution to the ferric chloride solution (at a rate of less than 20 mL/min) using an addition funnel and control the temperature of the reaction mixture below 40° C. using the water bath and the rate of addition of sodium hydroxide.
  Continue to cool the brown viscous mixture to below 30° C. using the water bath.
  The final pH should be above 7. Use a suitable volume of 5 M aqueous sodium hydroxide solution to correct the pH if not above 7. Measure and record the final pH. A dark brown precipitate of ferric hydroxide is formed.
  If required, cool the brown viscous mixture to below 30° C. using the cold water bath and filter the ferric hydroxide suspension through 1 mm size stainless steel filter to break up large precipitates.
  Transfer equal amounts of ferric hydroxide suspension into four 500 mL centrifuge containers. Balance the weight of each centrifuge container using a top-loading balance before centrifugation.
  Centrifuge the ferric hydroxide suspension at 1500 rpm and 25±5° C. for 5 minutes. Discard the supernatant.
  Measure 2.5 L of deionized water using a graduated cylinder and use approximately 1 L of water to re-suspend the ferric hydroxide precipitate from the centrifuge containers.
  Transfer the ferric hydroxide suspension into a 4 L Erlenmeyer flask fitted with a 1 mm size stainless steel filter over a glass funnel. Use the remaining 1.5 L of deionized water to rinse the containers and wash the precipitate retained on the stainless steel filter.
  Wash the precipitate two more times by repeating the steps beginning with "Transfer equal amounts . . . "
  After the third wash, recover the precipitate by repeating the steps beginning with "Transfer equal amounts . . . " and ending with "Centrifuge the ferric hydroxide suspension . . . "
  Re-suspend the precipitate in 150 mL of deionized water.

4.4. Preparation of Ferric Citrate
  Homogenize the ferric hydroxide precipitate using a mechanical stirrer for 5 min in a 2 L Erlenmeyer flask.

Weigh 490 g of citric acid (correct for CoA purity) into a 500 mL beaker.

Place a stir bar in the 2 L Erlenmeyer flask in an oil bath and stir at high speed.

Add the citric acid into the ferric hydroxide suspension. Stir the solution for 30 minutes.

Heat the mixture at 90 to 100° C. (in oil bath) until the color changes from orange-brown to a clear black-brown (for 30 to 120 mm) or until ferric hydroxide precipitate is dissolved.

Take 1 mL aliquot of the reaction mixture in a 6 mL glass test tube and centrifuge at 1500 rpm and 25±5° C. for 5 minutes. Proceed to the next step if no precipitate is observed. If some precipitate is observed add 10 to 34 g citric acid to the mixture and continue heating for 10 to 30 min.

Terminate the heating and cool the mixture to below 30° C. Measure the pH of the reaction mixture; it should be pH 0.8 to 1.5.

Transfer equal amounts of the reaction mixture into four 500 mL centrifuge containers and balance the weight of each container using a top-loading balance.

Centrifuge the reaction mixture at 1500 rpm and 25±5° C. for 5 minutes. Transfer and pool all the ferric citrate supernatant to a clean 4 L Erlenmeyer flask.

Repeat the above 2 steps for all of the ferric citrate reaction mixture.

Place one-half of the ferric citrate supernatant in a 4 L Erlenmeyer flask and stir with a magnetic stir bar at high speed.

Add slowly (over 20 min.) 3.5 L of acetone (accurate volume acetone calculated as five fold the supernatant volume) and stir for an additional 10 min. A light-beige color precipitate forms.

Transfer the suspension into four 500 mL centrifuge containers and balance the weight of each container using a top-loading balance.

Centrifuge the ferric citrate suspension at 1500 rpm and 25±5° C. for 5 minutes.

Transfer and pool all the ferric citrate precipitate to a clean 4 L Erlenmeyer flask.

Repeat the above 4 steps with the second half of the ferric citrate supernatant.

Pool all ferric citrate precipitate, add 1.4 L of acetone and stir for 5 min.

Transfer the suspension into four 500 mL centrifuge containers and balance the weight of each container using a top-loading balance.

Centrifuge the suspension at 1500 rpm and 25±5° C. for 5 minutes.

Repeat the above 2 steps until all suspension is centrifuged.

Transfer and pool all the ferric citrate precipitate to a clean 4 L Erlenmeyer flask.

Repeat the above 5 steps two additional times (total of 3 washes).

Label and weigh drying trays, and record their weight.

Transfer the ferric citrate precipitate onto the drying dishes and dry at ambient temperature (25±5° C.) for 16 hours.

Place the drying trays with precipitate into a vacuum oven and dry at ambient temperature (25±5° C.) and under vacuum (about 20 mm Hg) for 8 to 16 hours (until the material appears ready for grinding).

Reduce the particle size of the ferric citrate in a porcelain mortar and pestle.

Place the ferric citrate powder into a vacuum oven and dry at ambient temperature (25±5° C.) and under vacuum (about 20 mm Hg) for 8 to 24 hours, until the material appears ready for sieving.

Finely reduce the ferric citrate particle size in a porcelain mortar and pestle. Screen the ferric citrate powder through a 45 mesh size (355 micron) sieve.

Transfer the ferric citrate powder into drying trays and place the trays in an oven to dry at 25±5° C. and under high vacuum until the material appears dry (20 to 48 hours).

Transfer the powder into pre-weighed plastic amber containers.

Label and store the containers at ambient temperature and protected from light.

Example 5

Method for Scalable Manufacture of Pharmaceutical-Grade Ferric Citrate

Figure 3:
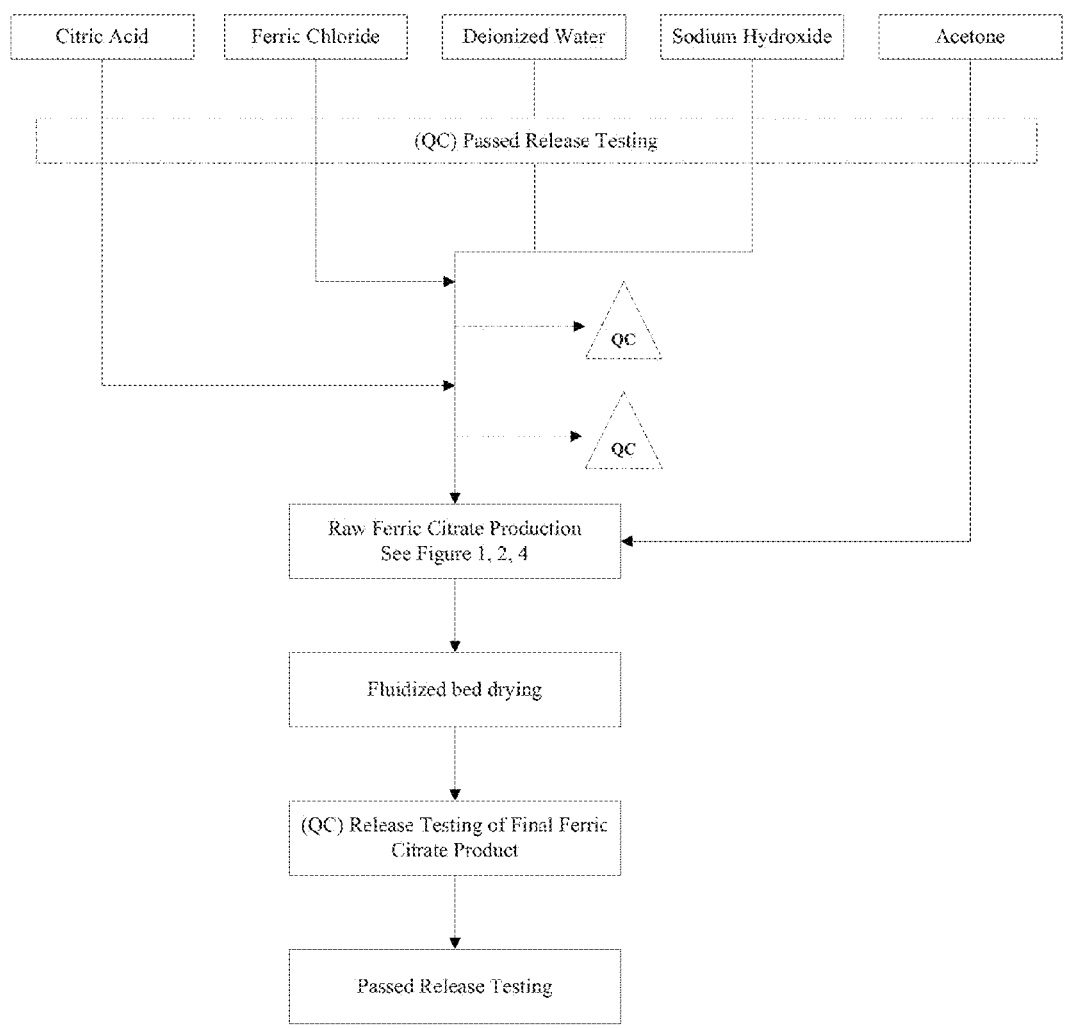
FIG. 3 shows an overview of scalable pharmaceutical-grade ferric citrate manufacturing and quality control process according to the invention.
Figure 4:
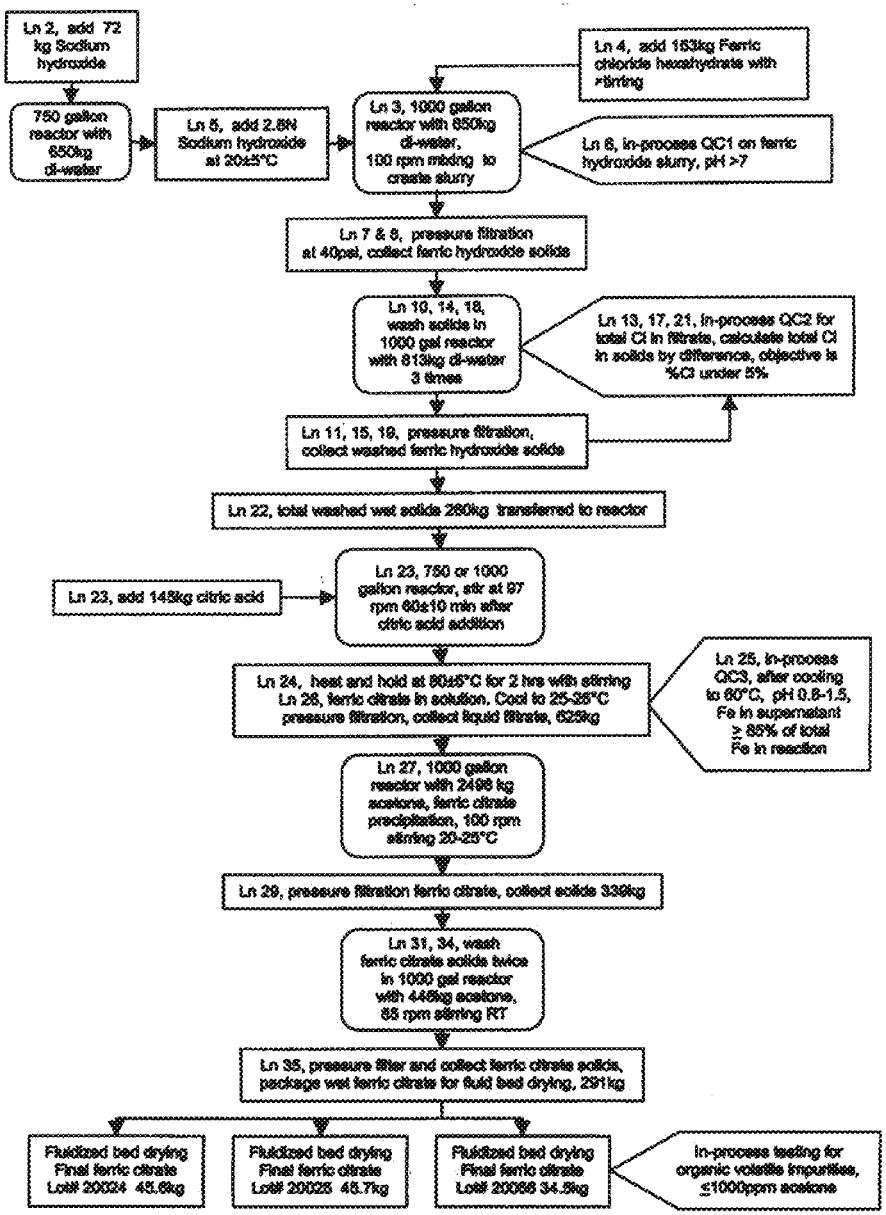
FIG. 4 is a schematic diagram of scalable pharmaceutical-grade ferric citrate manufacturing and quality control process according to the invention.
Figure 5:
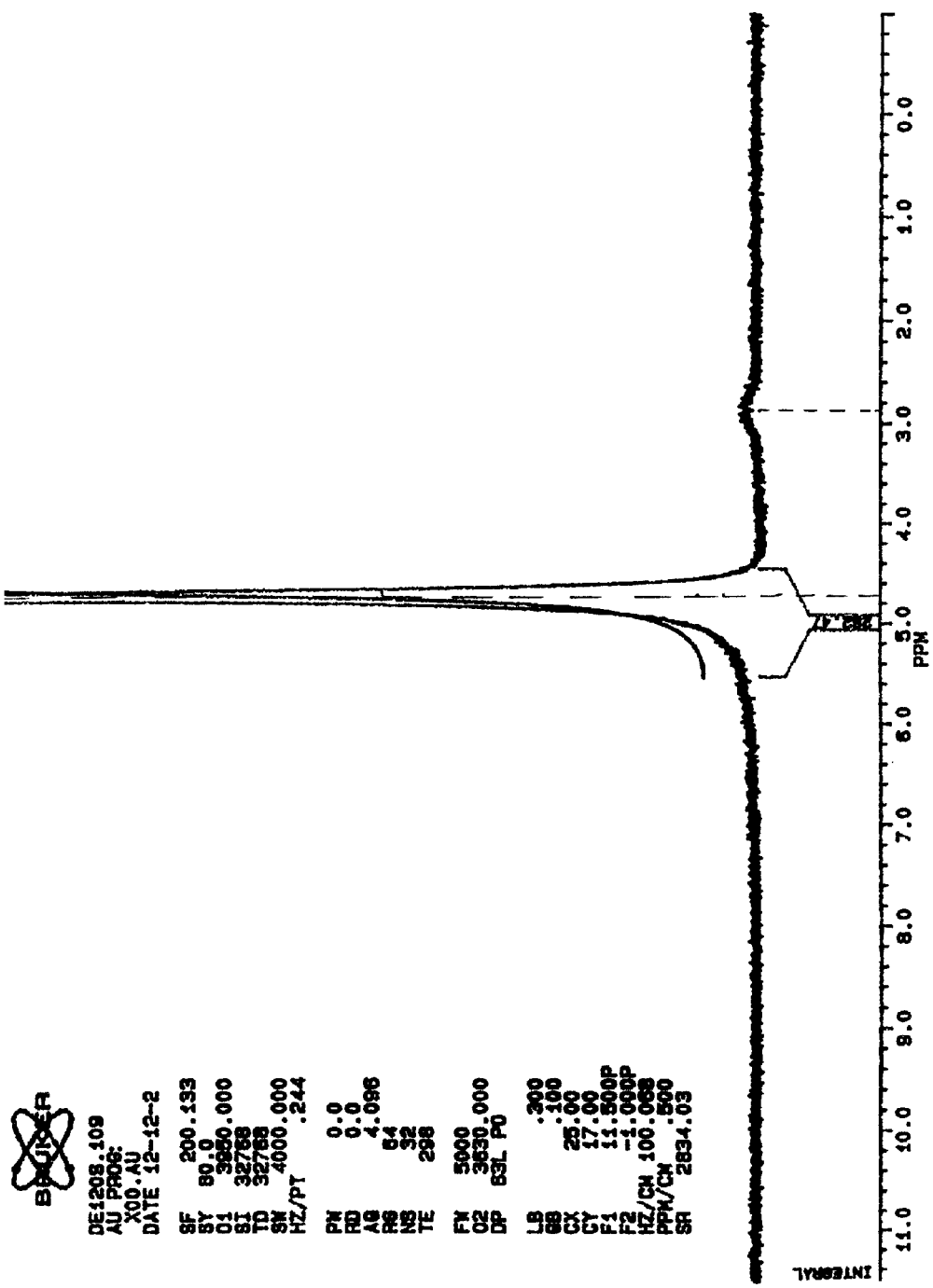
FIG. 5 shows the representative proton NMR spectrum for a pharmaceutical-grade ferric citrate according to the invention.

The present invention provides a scalable manufacturing of pharmaceutical-grade ferric citrate. Preferably, the ferric citrate manufacturing process is capable of producing at least 125 kg batches of pharmaceutical-grade ferric citrate. An overview of the ferric citrate manufacturing is shown in FIG. 3. Details of the synthesis of ferric citrate are shown in FIG. 4.

The scalable manufacturing process further employs fluidized bed dryer for drying wet ferric citrate and for attaining release specifications for organic volatile impurities. See Table A for the Manufacture Release Specifications for Pharmaceutical-Grade Ferric Citrate.

Example 6

A Pharmaceutical-Grade Ferric Citrate

This invention provides a pharmaceutical-grade ferric citrate which complies with the Manufacture Release Specifications as shown below in Table A. The pharmaceutical-grade ferric citrate of consistent purity and quality can be prepared using the manufacturing process of the present invention. See FIGS. 1-4 for the schematic diagram of the ferric citrate manufacturing and quality control process. The ferric citrate manufacturing and quality control process can be readily scaled to produce multi-kilogram batch sizes or scaled up to a manufacturing scale.

TABLE A

Manufacture Release Specification for Pharmaceutical-Grade Ferric Citrate

| Test Item | Method | Limit of Specification |
|---|---|---|
| Appearance | Visual | Light brown to beige powder |
| Purity of solid state ferric citrate | Calculate based on LC/MS - flow injection quantitation and profile, based on USP 25 <621>, <731>, <1086>, <736> | NLT 90% w/w anhydrous basis |
| Assay content of ferric citrate non-related | LC/MS - flow injection profile, based on USP 25 <621>, <731>, | Run and report as % w/w anhydrous basis |

TABLE A-continued

Manufacture Release Specification for Pharmaceutical-Grade Ferric Citrate

| Test Item | Method | Limit of Specification |
|---|---|---|
| substances in solution state | <1086>, <736> | (attach table summary) |
| Assay content purity of ferric citrate and water adduct in solution state | LC/MS - flow injection quantitation, based on USP 25 <621>, <731>, <1086>, <736> | NLT 70% w/w anhydrous basis |
| Assay content of citric acid related substance in solution state | LC/MS - flow injection quantitation, based on USP 25 <621>, <731>, <1086>, <736> | NLT 10% w/w anhydrous basis |
| Assay content of other ferric citrate related substances in solution state (excluding citric acid) | LC/MS - flow injection profile, based on USP 25 <621>, <731>, <1086>, <736> | Run and report as % w/w anhydrous basis (attach table summary) |
| Assay content of ferric iron | Based on USP 25 ferric sulfate assay | NLT 16% w/w fresh weight basis |
| Limit of ferrous iron | Gravimetric method using potassium ferricynide, based on USP 25 <191> | NMT 1% w/w fresh weight basis |
| Loss on drying | USP 25 <731> | NMT 20% |
| Hydrate (water content) | Karl Fischer Titration USP 25 <921> water determination, Method Ia (Direct Titration) | NMT 20% |
| Identification | Method A: based on USP 25 <191> ferric salt | Dark blue precipitate with $K_4Fe(CN)_6$ TS; reddish brown ppt with excess 1N NaOH; deep red color not destroyed by mineral acids with $NH_4SCN$ TS Sample solution gives light red color with pyridine and acetic anhydride |
| Limit of chloride | Based on USP 25 Ferric sulfate procedures | NMT 5% |
| Reside on ignition | Modified USP 25 <281> | Run and report |
| Organic Volatile Impurities | Based on USP 25 <467> | Acetone not more than 1000 ppm |
| Limit of acid insoluble substances | Gravimetric determination, based on USP 25, ferric sulfate | Not more than 0.02% w/w fresh weight basis |
| Trace/heavy metals | USP 25 method <231> or equivalent ICP for Zn, Cu, Sr, Ca, Na GFAAS for As | As <0.3 ppm Others: run and report |
| Lead, Cadmium | ICP-MS | Pb <5 ppm Cd <2 ppm |
| Mercury | Cold vapor/AA | Hg <0.3 ppm |
| Total iron content | ICP | NLT 16% w/w fresh weight basis |
| Microbial/Mold and Yeast | USP Method <61> *Salmonella* *E. Coli* Coliforms Total aerobic count Total combined mold and yeast | *Salmonella* = negative *E. Coli* = negative Total Coliforms <3 cfu/g Total aerobic count <10 cfu/g Total mold and yeast <20 cfu/g |

Example 7

Raw Material Release Testing Specifications

TABLE B

Ferric chloride hexahydrate Release Specifications

| Test Item | Method | Limit of Specification |
|---|---|---|
| Appearance | Visual | Yellow to yellowish brown powder, crystals or chunks |
| Identification - Ferric salts | USP 25 <191> | Yield dark blue precipitate with potassium ferrocyanide TS Form reddish brown precipitate with excess 1N NaOH Red deep color with ammonium thiocyanate TS and color not destroyed by dilute mineral acids |
| Identification - Chloride | USP 25 <191> | Aqueous solution of ferric chloride yields with 0.1N silver nitrate TS a white, cruddy precipitate, which is insoluble in nitric acid but is soluble in a slight excess of 6N ammonium hydroxide |

TABLE B-continued

Ferric chloride hexahydrate Release Specifications

| Test Item | Method | Limit of Specification |
|---|---|---|
| Heavy metals | ICP-MS | As <0.1 ppm<br>Cd <0.1 ppm<br>Hg <0.1 ppm<br>Pb <0.1 ppm |
| Assay - Ferric iron | USP 25, Assay ferric sulfate, p. 2303 | >18% |

TABLE C

Sodium Hydroxide Release Specifications

| Test Item | Method | Limit of Specification |
|---|---|---|
| Appearance Identification - Sodium | Visual USP25, <191> | White pellets, odorless<br>No precipitate is formed with potassium carbonate<br>A dense precipitate is formed with potassium pyroantimonate<br>An intense yellow color to a non-luminous flame |

TABLE D

Deionized Water Release Specification

| Test Item | Method | Limit of Specification |
|---|---|---|
| Appearance | Visual | Clear, colorless and odorless |
| Mineral scan | ICP-MS | As <0.001 ml/L<br>Cd <0.0002 ml/L<br>Pb <0.001 ml/L<br>Hg <0.02 µg/L |
| Total Organic Carbon | Standard Method for the Examination of Water and Wastewater, 20$^{th}$ ed. | <1 mg/L |
| Total Hardness | Standard Method for the Examination of Water and Wastewater, 20$^{th}$ ed. | <4 mg/L |
| Total Plate Count | USP 25 method <61> | <10 cfu |
| Total Coliform Count | USP 25 method <61> | <3 cfu |

TABLE E

Acetone Release Specification

| Test Item | Method | Limit of Specification |
|---|---|---|
| Appearance Identification - Acetone | Visual USP 25, p.2502, FTIR | Clear colorless liquid<br>The IR absorption of a thin film between KBr plates exhibits a strong band at about 5.8 µm; a strong region of absorption between 6.8 and 7.5 µm, with maxima at about 7.0 and 7.3 µm; a strong maximum at about 8.2 µm; and a weak maxima at about 9.2 and 11.0 µm. |
| Assay | From manufacturer's Certificate of Analysis (result from GC method preferred) | NLT 99.5% |
| Aldehyde (as HCHO) | From manufacturer's Certificate of Analysis | NMT 0.002% |
| Isopropyl alcohol | From manufacturer's Certificate of Analysis | NMT 0.05% |
| Methanol | From manufacturer's Certificate of Analysis | NMT 0.05% |
| Residue after evaporation | From manufacturer's Certificate of Analysis | NMT 5 ppm |
| Acids | From manufacturer's Certificate of Analysis (result from titrimetric test) | NMT 0.0003 meq |
| Bases | From manufacturer's Certificate of Analysis (result from titrimetric test) | NMT 0.0006 meq |
| Water | From manufacturer's Certificate of Analysis | NMT 2% |
| Insoluble substances | From manufacturer's Certificate of Analysis or filtered through ≤0.45 µm filter | filtered through ≤0.45 µm filter |

TABLE F

Citric Acid Release Specification

| Test Item | Method | Limit of Specification |
|---|---|---|
| Appearance | Visual | White or colorless crystals or powder |
| Identification - Citrate | USP 25 <191> | A light red color is produced |

Example 8

Final Product Manufacture Release Testing Methods

The following tests are performed to ensure the final ferric citrate product prepared according to the method or process of the present invention complies with the established Manufacture Release Specification as shown in Table A. The Manufacture Release Specification may be readily modified or revised by one of ordinary skill in the art following the teaching of this invention to enhance the purity and safety of the pharmaceutical-grade ferric citrate for human use.

(a) Based on USP 25 <191> Gravimetric method using potassium ferricyanide, p. 1918—Limit of Ferrous Iron in Ferric Citrate
(b) Based on USP 25, ferric sulfate assay, p. 728—Limit of Chloride in Ferric Citrate
(c) Based on USP 25, ferric sulfate assay, p. 728—Limit of Acid Insoluble Substances in Ferric Citrate
(d) Based on USP 25, ferric sulfate assay, p. 728—Assay Content of Ferric Iron in Ferric Citrate
(e) Based on USP 25 <467>—Determination of Acetone in Ferric Citrate Samples by GClFID Headspace
(f) Based on USP 25 <191> Ferric Salts; Citrate, p. 1918 —Identification of Ferric Citrate
(g) Based on USP 25 <621>, p. 1988-1995, <731>, <1086>, p. 2157-2159, <736>, p. 2029-2033—LCMS Flow-Injection Quantitation and Profile of Ferric Citrate and Related Substances
(h) USP 25 <731> Loss on Drying
(i) USP 25 <921> Water Determination, Method Ia (Direct Titration)
(j) ICP for Zn, Cu, Sr, Ca, Na and total iron
(k.) GFAAS for As
(l) TCP-MS for lead and cadmium
(m) Cold vapor/AA for mercury
(n) Residue on ignition
(o) Microbial/mold and yeast Example 9

Methods of Using and Testing the Pharmaceutical-Grade Ferric Citrate in Patients In Vivo A. Handling and Forms of Test Compositions Ferric citrate is supplied in 500 mg capsules, whereas the placebo will be provided in identical-looking capsules (indistinguishable from those containing the active drug); the placebo capsules will contain sorbitol and colorant to match the powder color of the active capsules. The placebo capsule shells will be identical to the active capsule shells.

Storage

All study drug supplies must be stored under secure conditions and are not to be used after their expiration date, which is imprinted on the study drug container. The study drugs should be kept, under controlled conditions (15 to 30° C.; 59 to 86° F.) in a tightly closed container, protected from light.

Dosage

A recent pilot study compared ferric citrate (3 g daily) to calcium carbonate (3 g daily) for reducing serum $PO_4$ in patients with End Stage Renal Disease (ESRD). Although ferric citrate caused a significant decrease in serum P04, it was not as effective as calcium carbonate. This dose of ferric citrate was associated with mild, hut tolerable GI symptoms.

As shown in FIGS. 12 and 13, treatments using pharmaceutical-grade ferric citrate provide several advantages over chemical grade ferric citrate. In general, while pharmaceutical-grade ferric citrate demonstrates an efficacy approximately equal so that of chemical grade ferric citrate, it achieves this result with less adverse side effects than chemical grade ferric citrate.

FIG. 12 also indicates chat adverse side effects associated with administering pharmaceutical-grade ferric citrate were not statistically different from chose associated with the placebo. An advantage of this safety profile is that an individual patient may have his dosing of pharmaceutical-grade ferric citrate titrated over a broad range of doses with less concern about side effect. In this way, a patient's individual treatment may be tailored to suit his specific needs and tolerances.

The doses of ferric citrate chosen for study or treatment may be from 1 to 30 grams of ferric citrate per day. In part, this may depend on the nature of the formulation provided. For example, ferric citrate capsules may be administered up to a daily dose of about 15 grams/day, whereas the tablet form may be administered up to 30 grams/day. Thus, there is a very broad range of dosing regimens encompassed by the invention.

Titration of Optimal Dosage for a Subject

In the context of this invention, the term "subject" refers to either a human or non-human animal.

The optimal dosage of an individual subject or groups may be determined as follows. A dose of approximately one or two grams per day is merely suggested as an illustrative starting dose. The daily dose may be increased as needed until the desired result is observed.

The intent of the invention is to not limit the dose range employed. Therefore, depending on the subject(s) the daily dose administered may approximate thirty, forty, fifty, sixty, seventy, eighty, ninety or one hundred grams per day. The safety profile of the pharmaceutical-grade ferric citrate allows the implementation of a broad range of doses.

Further, it is the intent of the invention to not be limited to capsules and tablets as oral formulations. It is known in the art that a wide variety of oral formulations may be adapted for use with the invention.

Illustrative Example of a Dosage Regimen

An non-limiting example of a dosing regimen is provided below. This is not meant to limit the invention as to how an effective amount of ferric citrate is selected, or the form in which it is provided or the frequency of administering the composition per day. The following merely illustrates how ferric citrate and placebo may be administered; e.g., as 500 mg capsules of identical appearance. All patients may receive (in a blinded fashion) 4 capsules with each of three meals, on a daily basis, for 28 days. Patients will be instructed to take the study medication within 10 minutes of finishing their meals (breakfast, lunch, and dinner).

The number of placebo, and active capsules to be taken at each meal, are as follows:

Placebo Arm of the Study
4 placebo capsules, with breakfast.
4 placebo capsules, with lunch.
4 placebo capsules with dinner
Ferric Citrate 2 g Per Day Arm of the Study
1 ferric citrate capsule and 3 placebo capsules with breakfast
1 ferric citrate capsule and 3 placebo capsules with lunch
2 ferric citrate capsules and 2 placebo capsules with dinner
Ferric Citrate 4 g Per Day Arm
2 ferric citrate capsules and 2 placebo capsules with breakfast
3 ferric citrate capsule and 1 placebo capsule with lunch
3 ferric citrate capsules and 1 placebo capsule with dinner
Ferric Citrate 6 g Per Day Arm
4 ferric citrate capsules with breakfast
4 ferric citrate capsules with lunch
4 ferric citrate capsules with dinner
B. Clinical Schedule and Assessments
Duration of Study Treatment Each patient's participation in the trial lasts for up to 8 weeks: the screening period (approximately 1-2 weeks), a 1-2 week washout, and 4 weeks of treatment with study medication.

Screening Visit 1 (Study Days −30 to −15)

The following procedures will be performed at the first screening visit:
1. Medical history, including concomitant medications.
2. Demographic data
3. Physical examination, including height, weight, and vital signs.

4. Dietary interview, using 24 hour recall method, to assess dietary intake of calcium and phosphorous, three times during screening period, to include one dialysis day, one non-dialysis day, and one weekend day. Note: Dietary interview may be also performed, in part or in whole, during the washout period.
5. Laboratory assessment:
   Hematology: complete blood count (CPU) with differential, platelets.
   Chemistries: sodium, potassium, chloride, bicarbonate, blood urea nitrogen (BUN), creatinine, glucose (random), aspartate transaminase (AST), alanine transaminase (ALT), alkaline phosphatase (ALP), total bilirubin, total protein, albumin, serum calcium, serum phosphate, magnesium
   Total and LDL cholesterol levels
   Serum (3-HCG for women of childbearing potential
   Iron panel: serum iron, ferritin, transferrin saturation percentage, and total iron binding capacity.
6. 12-lead ECG,
7. Patients will be given instructions for the Washout Period (Study Days −14 to −1):
a. All phosphate-binding agents will be discontinued at Day −14
b. Any iron therapy (oral or intravenous) will be discontinued at Day −14
c. Patients who have been receiving a stable dose of vitamin D or calcitriol for 1 month prior to enrollment will be instructed to maintain their current dose throughout the study
d. Patients will be advised to avoid changes in diet, calcium or magnesium containing antacids (other medications).

Screening Visit 2 (Study Days −7+/−1 Day)
1. Laboratory Assessment:
Serum $PO_4$
Note: Patients with a Day −7 serum $PO_4 \geq 5.5$ mg/dL and ≤10 mg/dL may be randomized before the 2-week washout is complete. The day of randomization will automatically become Day 0.
Note: Patients with a Day −7 phosphate level of ≤10 mg/dL will be removed from the study and instructed to resume their pre-study medications.

Study Day 0 (Randomization And Dosing)
1. Physical examination, including weight and vital signs.
2. Adverse event query.
3. Concomitant medication query.
4. Baseline Laboratory assessments:
   Serum P04
   Serum Ca
   Iron panel: serum iron, ferritin, transferrin saturation percentage, and total iron binding capacity
Note: The Baseline Laboratory Assessments may be done up to 3 days prior to Day 0
5. Patients with a $PO_4$ level ≥0.5 mg/dL and ≤10 mg/dL will be randomized and a 15-day supply of study medication will be dispensed.
Note: Patients should be instructed to begin taking study medication within 10 minutes of completing their next meal on Day 0.

Study Day 1.4 (Midpoint Evaluation)
The following procedures will, be performed at Study Day 14+/−1 day.
1. Physical examination including weight and vital signs.
2. Adverse event query.
3. Concomitant medication query.
4. Dispense an additional 15-day supply of study medication.
All returned capsules should be counted and recorded in the Case Report Form.
5. Laboratory assessment:
   Hematology: CBC with differential, platelets.
   Chemistries: sodium, potassium, chloride, bicarbonate, BUN, creatinine, glucose (random), AST, ALT, ALP, total bilirubin, total protein, albumin, calcium, phosphate, magnesium.
   Iron panel: serum iron, ferritin, transferrin saturation percentage, and total iron binding capacity.
   Total and LDL cholesterol levels.
Note: Patients with a Day 14 phosphate level of >10 mg/dL will be removed from the study and instructed to resume their pre-study medications.

Study Day 28 (End Of Study Evaluation)
The following procedures will be performed at Study Day 28+/−1 day or on the day of early termination.
1. Physical examination including weight and vital signs
2. Adverse event query.
3. Concomitant medication query.
4. Laboratory assessment:
   a. Hematology: CBC with differential, platelets
   b. Chemistries: sodium, potassium, chloride, bicarbonate, BUN, creatinine, glucose (random), AST, ALT, ALP, total bilirubin, total protein, albumin, calcium, phosphate, magnesium.
   c. Total and LDL cholesterol levels
   d. Iron panel: serum iron, ferritin, transferrin saturation percentage, and total iron binding capacity.
5. 12-lead ECG
6. Patients will be instructed to resume their pre-study medications after completing the study.

C. Data Management and Analysis
GloboMax will be the primary data management, monitoring, and coordinating center. Case report forms (CRF) will be provided for each subject. Subjects will not be identified by name or initials on CRFs. The CRF will be monitored at the clinical sites and collected by GloboMax's study monitor. Audited CRFs will be used to create electronic data files.

Three major categories of endpoints reflect biochemical and clinical issues being addressed at the outset. Additional clinical and biochemical issues are addressed as they arise. Therefore, the endpoints are not meant to limit the totality of relevant findings and measurements collected in these, or future studies.

Primary Endpoints (see FIGS. 9-10)
The change in serum $PO_4$ concentration at Days 14 and 28 from baseline.
Secondary Endpoints (see FIGS. 9-10)
The change in serum calcium concentration at Days 14 and 28 from baseline.
The change in iron, ferritin, transferrin saturation percentage, and total iron binding capacity at Days 14 and 28 from baseline.
The change in the $Ca'PO_4$ product at Days 14 and 28 from baseline.

It is further noted chat in comparison to chemical grade ferric citrate, the pharmaceutical grade ferric citrate demonstrates similar efficacy. See FIG. 13. However, the safety profiles indicate that the pharmaceutical grade generally results in less adverse clinical effects. See FIG. 13.

Safety Endpoints (see FIG. 11)
Safety will be monitored by recording adverse events (FIG. 11) and the results of physical examinations, vital signs and laboratory tests at each study visit.
Specific rules for withdrawal from the study, based on laboratory data, have also been set up so ensure patient safety. A nonlimiting example of such criteria is illustrated by the following:

If a patient's serum phosphate level increases to ≥10 mg/dL at any time during the study period, the patient will be withdrawn from the study.

Specific studies have also shown that pharmaceutical grade ferric citrate possesses similar efficacy to chemical grade ferric citrate. (See FIG. 13). However, the pharmaceutical grade generally affords a significantly more desirable safety profile as shown in FIG. 12. This indicates an important advance in regulating serum phosphate levels.

What is claimed is:

1. A pharmaceutical composition comprising a form of ferric citrate having an intrinsic dissolution rate of 1.88-4.0 mg/cm$^2$/min and a pharmaceutically suitable carrier, wherein the ferric citrate is present in an amount effective to reduce serum phosphate levels.

2. The pharmaceutical composition of claim 1, wherein the effective amount of ferric citrate is from 2 grams per day to 30 grams per day.

3. The pharmaceutical composition of claim 1, wherein the effective amount of ferric citrate is from 4 grams per day to 15 grams per day.

4. The pharmaceutical composition of claim 1, wherein the effective amount of ferric citrate is from 2 grams per day to 12 grams per day.

5. The pharmaceutical composition of claim 1, wherein the effective amount of ferric citrate is selected from 2 grams per day, 4 grams per day and 6 grams per day.

6. The pharmaceutical composition of claim 1, wherein the effective amount of ferric citrate is 1 gram per day.

7. The pharmaceutical composition of claim 1, wherein the effective amount of ferric citrate is 500 mg per unit dosage form.

8. A pharmaceutical composition comprising 500 mg of a form of ferric citrate having an intrinsic dissolution rate of 1.88-4.0 mg/cm$^2$/min, and a pharmaceutically suitable carrier, wherein the pharmaceutical composition is in a capsule dosage form.

* * * * *

UNITED STATES PATENT AND TRADEMARK OFFICE
CERTIFICATE OF CORRECTION

PATENT NO.        : 8,754,257 B2  
APPLICATION NO.   : 13/661558  
DATED             : June 17, 2014  
INVENTOR(S)       : Keith Chan and Winston Town Page 1 of 1

It is certified that error appears in the above-identified patent and that said Letters Patent is hereby corrected as shown below:

Title Page

Item (71) Applicant, please replace "GloboAsia, LLC, Rockville, MD (US)" with --Panion & BF Biotech, Inc., Taipei (TW)--

On page 2, Item (56) under "FOREIGN PATENT DOCUMENTS", please replace "ID WO2005002228" with --ID W00200502228--

Signed and Sealed this  
Sixteenth Day of September, 2014

Michelle K. Lee  
*Deputy Director of the United States Patent and Trademark Office*